US006416988B1

(12) United States Patent
Conklin et al.

(10) Patent No.: US 6,416,988 B1
(45) Date of Patent: Jul. 9, 2002

(54) BETA-1,3-GALACTOSYLTRANSFERASE HOMOLOGS

(75) Inventors: Darrell C. Conklin; Gayle Yamamoto, both of Seattle; Stephen R. Jaspers, Edmonds; Zeren Gao, Redmond, all of WA (US)

(73) Assignee: Zymogenetics, Inc., Seattle, WA (US)

( * ) Notice: Subject to any disclaimer, the term of this patent is extended or adjusted under 35 U.S.C. 154(b) by 0 days.

(21) Appl. No.: 09/459,133

(22) Filed: Dec. 10, 1999

Related U.S. Application Data

(60) Provisional application No. 60/111,697, filed on Dec. 10, 1998.

(51) Int. Cl.[7] .......................... C12N 9/10; C12N 15/00; C12N 5/00; C12N 1/20; C07H 21/04
(52) U.S. Cl. .................. 435/193; 536/23.2; 435/320.1; 435/325; 435/252.3
(58) Field of Search .............................. 435/320.1, 325, 435/252.3, 193; 536/23.2

(56) References Cited

U.S. PATENT DOCUMENTS 5,955,282 A    9/1999   Hillman et al. ................ 435/6

OTHER PUBLICATIONS

Amado, et al., *Journal of Biological Chemistry* 273:21, 12770–12778, 1998.
Shur, B.D., *Molecular and Cellular Biochemistry* 61: 143–158, 1984.
Goode, S., *Development al Biology 178*: 35–50, 1996.
Berger, E.G., *TCB* 2:103–108, 1994.
Mashima, H. et al., *Endocrinology 137*: 3969–3976, 1996.
Public EST, EST1744894, 1998.
Public EST, EST2685698, 1999.
Public EST, EST2324537, 1999.
Public EST, EST2265415, 1999.
Public EST, EST828755, 1997.
Incyte Pharmaceuticals EST, INC732535, 1996.
Incyte Pharmaceuticals EST, INC1693149, 1996.
Incyte Pharmaceuticals EST, INC1638748, 1996.
Incyte Pharmaceuticals EST, INC1632867, 1996.
Incyte Pharmaceuticals EST, INC1633313, 1996.
Incyte Pharmaceuticals EST, INC1719677, 1996.
Incyte Pharmaceuticals EST, LIN1803159T6, 1997.
Incyte Pharmaceuticals EST, LIN1803159F6, 1997.
Incyte Pharmaceuticals EST, INC3222690, 1997.
Incyte Pharmaceuticals EST, INC3773358, 1997.
Incyte Pharmaceuticals EST, INC4876646, 1998.
Incyte Pharmaceuticals EST, INC1893492, 1999.

*Primary Examiner*—Rebecca E. Prouty
*Assistant Examiner*—David J. Steadman
(74) *Attorney, Agent, or Firm*—Robyn Adams

(57) ABSTRACT

The present invention relates to polynucleotide and polypeptide molecules for znssp2, a novel member of the galactosyltransferase family. The polypeptides, and polynucleotides encoding them, are cell-cell interaction and glycoprotein synthesis modulating and may be used for delivery and therapeutics. The present invention also includes antibodies to the znssp2 polypeptides.

7 Claims, No Drawings

SEQUENCE LISTING

<160> NUMBER OF SEQ ID NOS: 20

<210> SEQ ID NO 1
<211> LENGTH: 1532
<212> TYPE: DNA
<213> ORGANISM: Homo sapiens
<220> FEATURE:
<221> NAME/KEY: CDS
<222> LOCATION: (101)...(1294)

-continued

```
<400> SEQUENCE: 1
atcagaggga gctgagggag gcctgacctg aggccggcac ccggagctgg cgggagccag      60
acccagagct cccgcggccg ccccttccct gggtcgggtc atg cgc tgc ccc aag      115
                                             Met Arg Cys Pro Lys
                                              1               5 tgc ctt ctc tgc ctg tca gca ctg ctc aca ctc ctg ggc ctc aaa gtg      163
Cys Leu Leu Cys Leu Ser Ala Leu Leu Thr Leu Leu Gly Leu Lys Val
             10                  15                  20 tac atc gag tgg aca tcc gag tcc cgg ctc agc aag gcc tac ccc agc      211
Tyr Ile Glu Trp Thr Ser Glu Ser Arg Leu Ser Lys Ala Tyr Pro Ser
         25                  30                  35 cct cgg ggc acc ccg cca agc ccc acg cca gcc aac cct gag ccc acc      259
Pro Arg Gly Thr Pro Pro Ser Pro Thr Pro Ala Asn Pro Glu Pro Thr
     40                  45                  50 cta cct gcc aac ctc tcc acc cgc ctg ggc cag act atc ccg ctg ccc      307
Leu Pro Ala Asn Leu Ser Thr Arg Leu Gly Gln Thr Ile Pro Leu Pro
 55                  60                  65 ttt gct tac tgg aac cag cag cag tgg cgg ctg ggg tcc ctg ccc agt      355
Phe Ala Tyr Trp Asn Gln Gln Gln Trp Arg Leu Gly Ser Leu Pro Ser
 70                  75                  80                  85 ggg gac agc act gaa acg ggg ggc tgc cag gct tgg ggg gcc gcc gcc      403
Gly Asp Ser Thr Glu Thr Gly Gly Cys Gln Ala Trp Gly Ala Ala Ala
                 90                  95                 100 gcc acc gag atc cct gac ttc gcc tcc tac ccc aag gac ctc cgc cgc      451
Ala Thr Glu Ile Pro Asp Phe Ala Ser Tyr Pro Lys Asp Leu Arg Arg
            105                 110                 115 ttc ttg ctg tca gca gcc tgc cgg agc ttc cca cag tgg ctg cct gga      499
Phe Leu Leu Ser Ala Ala Cys Arg Ser Phe Pro Gln Trp Leu Pro Gly
        120                 125                 130 ggt ggt ggc rgc caa gtc tcc agc tgc tca gat act gat gtc ccc tac      547
Gly Gly Gly Xaa Gln Val Ser Ser Cys Ser Asp Thr Asp Val Pro Tyr
135                 140                 145 ctg ctg ttg gcc gtc aag tca gaa cca ggg cgc ttt gca gaa cga cag      595
Leu Leu Leu Ala Val Lys Ser Glu Pro Gly Arg Phe Ala Glu Arg Gln
150                 155                 160                 165 gcc gtg aga gag acg tgg ggc agt cca gct cca ggg atc cgg ctg ctc      643
Ala Val Arg Glu Thr Trp Gly Ser Pro Ala Pro Gly Ile Arg Leu Leu
            170                 175                 180 ttc ctg cta ggg tct ccg gtg ggt gag gcg ggg cct gac cta gac tca      691
Phe Leu Leu Gly Ser Pro Val Gly Glu Ala Gly Pro Asp Leu Asp Ser
        185                 190                 195 cta gtg gca tgg gag agc cgt cgc tac agt gac ctg ctc tgg gac          739
Leu Val Ala Trp Glu Ser Arg Arg Tyr Ser Asp Leu Leu Leu Trp Asp
    200                 205                 210 ttc ctc gac gtc cca ttc aac cag acg ctc aaa gac ctg ctg ctg ctg      787
Phe Leu Asp Val Pro Phe Asn Gln Thr Leu Lys Asp Leu Leu Leu Leu
215                 220                 225 gcc tgg ctg ggc cgc cac tgc ccc acc gtg agt ttt gtc ttg cga gct      835
Ala Trp Leu Gly Arg His Cys Pro Thr Val Ser Phe Val Leu Arg Ala
230                 235                 240                 245 cag gac gat gcc ttt gta cac acc cct gcc ctg ctg gct cac ctg cgg      883
Gln Asp Asp Ala Phe Val His Thr Pro Ala Leu Leu Ala His Leu Arg
            250                 255                 260 gcc ctg cca cct gcc tcg gcc cga agc ctc tac ctg ggt gag gtc ttt      931
Ala Leu Pro Pro Ala Ser Ala Arg Ser Leu Tyr Leu Gly Glu Val Phe
        265                 270                 275 acc cag gcc atg cct ctc cgg aag cca gga gga ccc ttc tat gtg ccc      979
Thr Gln Ala Met Pro Leu Arg Lys Pro Gly Gly Pro Phe Tyr Val Pro
    280                 285                 290
```

```
gag tcc ttc ttc gaa ggt ggc tac cca gcc tat gca agc ggg ggt ggc     1027
Glu Ser Phe Phe Glu Gly Gly Tyr Pro Ala Tyr Ala Ser Gly Gly Gly
    295                 300                 305 tac gtc att gcc ggg cgc ctg gca ccc tgg ctg ctg cgg gcg gca gcc     1075
Tyr Val Ile Ala Gly Arg Leu Ala Pro Trp Leu Leu Arg Ala Ala Ala
310                 315                 320                 325 cgt gtg gca ccc ttc ccc ttt gag gac gtc tac act ggc ctt tgc atc     1123
Arg Val Ala Pro Phe Pro Phe Glu Asp Val Tyr Thr Gly Leu Cys Ile
                330                 335                 340 cga gcc ctg ggc ctg gtg ccc cag gcc cac cca ggc ttc ctc aca gcc     1171
Arg Ala Leu Gly Leu Val Pro Gln Ala His Pro Gly Phe Leu Thr Ala
            345                 350                 355 tgg cca gca gac cgc act gcg gac cac tgt gct ttc cgc aac ctg ctg     1219
Trp Pro Ala Asp Arg Thr Ala Asp His Cys Ala Phe Arg Asn Leu Leu
        360                 365                 370 ctg gta cgg ccc ctg ggc ccc cag gcc agc att cgg ctc tgg aaa caa     1267
Leu Val Arg Pro Leu Gly Pro Gln Ala Ser Ile Arg Leu Trp Lys Gln
    375                 380                 385 ctg caa gac cca agg ctc cag tgc tga ctctcattgg ggagggcgga           1314
Leu Gln Asp Pro Arg Leu Gln Cys
390                 395 ggtgctgacc tggccccggc cctggcctgg gcctctgggg ccggcccctg gctcagcccc   1374
tccttccagg tcttgatggg agggaggagg gcccagaagc tggacaactt aagccactcc   1434
ttggcctccc ccagccaggg gcctgggcag gaaagatggg gtggtggact gttttgcct    1494 acttttgtt tttgaaaaac atgcactccc cactctga                            1532

<210> SEQ ID NO 2
<211> LENGTH: 397
<212> TYPE: PRT
<213> ORGANISM: Homo sapiens
<220> FEATURE:
<221> NAME/KEY: VARIANT
<222> LOCATION: (137)...(137)
<223> OTHER INFORMATION: Xaa is Gly or Ser
<220> FEATURE:
<221> NAME/KEY: VARIANT
<222> LOCATION: (1)...(397)
<223> OTHER INFORMATION: Xaa = Any Amino Acid

<400> SEQUENCE: 2

Met Arg Cys Pro Lys Cys Leu Leu Cys Leu Ser Ala Leu Leu Thr Leu
1               5                   10                  15

Leu Gly Leu Lys Val Tyr Ile Glu Trp Thr Ser Glu Ser Arg Leu Ser
                20                  25                  30

Lys Ala Tyr Pro Ser Pro Arg Gly Thr Pro Ser Pro Thr Pro Ala
            35                  40                  45

Asn Pro Glu Pro Thr Leu Pro Ala Asn Leu Ser Thr Arg Leu Gly Gln
50                  55                  60

Thr Ile Pro Leu Pro Phe Ala Tyr Trp Asn Gln Gln Trp Arg Leu
65                  70                  75                  80

Gly Ser Leu Pro Ser Gly Asp Ser Thr Glu Thr Gly Gly Cys Gln Ala
                85                  90                  95

Trp Gly Ala Ala Ala Thr Glu Ile Pro Asp Phe Ala Ser Tyr Pro
            100                 105                 110

Lys Asp Leu Arg Arg Phe Leu Leu Ser Ala Ala Cys Arg Ser Phe Pro
        115                 120                 125

Gln Trp Leu Pro Gly Gly Gly Xaa Gln Val Ser Ser Cys Ser Asp
    130                 135                 140
```

```
Thr Asp Val Pro Tyr Leu Leu Leu Ala Val Lys Ser Glu Pro Gly Arg
145                 150                 155                 160

Phe Ala Glu Arg Gln Ala Val Arg Glu Thr Trp Gly Ser Pro Ala Pro
                165                 170                 175

Gly Ile Arg Leu Leu Phe Leu Leu Gly Ser Pro Val Gly Glu Ala Gly
            180                 185                 190

Pro Asp Leu Asp Ser Leu Val Ala Trp Glu Ser Arg Arg Tyr Ser Asp
            195                 200                 205

Leu Leu Leu Trp Asp Phe Leu Asp Val Pro Phe Asn Gln Thr Leu Lys
        210                 215                 220

Asp Leu Leu Leu Ala Trp Leu Gly Arg His Cys Pro Thr Val Ser
225                 230                 235                 240

Phe Val Leu Arg Ala Gln Asp Asp Ala Phe Val His Thr Pro Ala Leu
                245                 250                 255

Leu Ala His Leu Arg Ala Leu Pro Pro Ala Ser Ala Arg Ser Leu Tyr
            260                 265                 270

Leu Gly Glu Val Phe Thr Gln Ala Met Pro Leu Arg Lys Pro Gly Gly
        275                 280                 285

Pro Phe Tyr Val Pro Glu Ser Phe Phe Glu Gly Tyr Pro Ala Tyr
290                 295                 300

Ala Ser Gly Gly Gly Tyr Val Ile Ala Gly Arg Leu Ala Pro Trp Leu
305                 310                 315                 320

Leu Arg Ala Ala Ala Arg Val Ala Pro Phe Pro Phe Glu Asp Val Tyr
                325                 330                 335

Thr Gly Leu Cys Ile Arg Ala Leu Gly Leu Val Pro Gln Ala His Pro
            340                 345                 350

Gly Phe Leu Thr Ala Trp Pro Ala Asp Arg Thr Ala Asp His Cys Ala
        355                 360                 365

Phe Arg Asn Leu Leu Val Arg Pro Leu Gly Pro Gln Ala Ser Ile
        370                 375                 380

Arg Leu Trp Lys Gln Leu Gln Asp Pro Arg Leu Gln Cys
385                 390                 395
```

<210> SEQ ID NO 3
<211> LENGTH: 1191
<212> TYPE: DNA
<213> ORGANISM: Artificial Sequence
<220> FEATURE:
<223> OTHER INFORMATION: Degenerate sequence
<220> FEATURE:
<221> NAME/KEY: misc_feature
<222> LOCATION: (1)...(1191)
<223> OTHER INFORMATION: n = A,T,C or G

<400> SEQUENCE: 3

```
atgmgntgyc  cnaartgyyt  nytntgyytn  wsngcnytny  tnacnytnyt  nggnytnaar    60
gtntayathg  artggacnws  ngarwsnmgn  ytnwsnaarg  cntayccnws  nccnmgnggn   120 acncencenw  snccnacnec  ngcnaayccn  garccnacny  tnccngcnaa  yytnwsnacn   180
mgnytnggnc  aracnathcc  nytnccntty  gcntaytgga  aycarcarca  rtggmgnytn   240
ggnwsnytnc  cnwsnggnga  ywsnacngar  acnggnggnt  gycargcntg  gggngcngcn   300
gcngcnacng  arathccnga  yttygcnwsn  tayccnaarg  ayytnmgnmg  nttyytnytn   360
wsngcngcnt  gymgnwsntt  yccncartgg  ytnccnggng  gnggnggnnn  ncargtnwsn   420
wsntgywsng  ayacngaygt  nccntayytn  ytnytngcng  tnaarwsnga  rccnggnmgn   480
```

-continued

```
ttygcngarm gncargcngt nmgngaracn tggggnwsnc cngcnccngg nathmgnytn    540
ytnttyytny tnggnwsncc ngtnggngar gcnggnccng ayytngayws nytngtngcn    600
tgggarwsnm gnmgntayws ngayytnytn ytntgggayt tyytngaygt nccnttyaay    660
caracnytna argayytnyt nytnytngcn tggytnggnm gncaytgycc nacngtnwsn    720
ttygtnytnm gngcncarga ygaygcntty gtncayacnc cngcnytnyt ngcncayytn    780
mgngcnytnc cnccngcnws ngcnmgnwsn ytntayytng gngargtntt yacncargcn    840
atgccnytnm gnaarccngg nggnccntty taygtnccng arwsnttytt ygarggnggn    900
tayccngcnt aygcnwsngg nggnggntay gtnathgcng gnmgnytngc nccntggytn    960
ytnmgngcng cngcnmgngt ngcnccntty ccnttygarg aygtntayac nggnytntgy   1020
athmgngcny tnggnytngt nccncargcn cayccnggnt tyytnacngc ntggccngcn   1080
gaymgnacng cngaycaytg ygcnttymgn aayytnytny tngtnmgncc nytnggnccn   1140
cargcnwsna thmgnytntg gaarcarytn cargayccnm gnytncartg y            1191

<210> SEQ ID NO 4
<211> LENGTH: 22
<212> TYPE: DNA
<213> ORGANISM: Artificial Sequence
<220> FEATURE:
<223> OTHER INFORMATION: Oligonucleotide primer, ZC18227

<400> SEQUENCE: 4
atcagaggga gctgagggag gc                                                22

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide primer, ZC17035

<400> SEQUENCE: 5
ggtctttgag cgtctggttg aatgg                                             25

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide primer, ZC16893

<400> SEQUENCE: 6
tacagtgacc tgctgctctg ggact                                             25

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide primer, ZC16894

<400> SEQUENCE: 7
cctgagctcg caagacaaaa ctcac                                             25

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide primer, ZC9719
```

-continued

```
<400> SEQUENCE: 8
actcactata gggctcgagc gcc                                              23

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide primer, ZC17035

<400> SEQUENCE: 9
ggtctttgag cgtctggttg aatgg                                            25

<210> SEQ ID NO 10
<211> LENGTH: 27
<212> TYPE: DNA
<213> ORGANISM: Artificial Sequence
<220> FEATURE:
<223> OTHER INFORMATION: Oligonucleotide primer, ZC9739

<400> SEQUENCE: 10
ccatcctaat acgactcact atagggc                                          27

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide primer, ZC17036

<400> SEQUENCE: 11
gaggaagtcc cagagcagca ggtca                                            25

<210> SEQ ID NO 12
<211> LENGTH: 1446
<212> TYPE: DNA
<213> ORGANISM: Mus musculus
<220> FEATURE:
<221> NAME/KEY: CDS
<222> LOCATION: (107)...(1273)

<400> SEQUENCE: 12
gcacagctgc gaggagggag tccggcaggg ctttacccga ggaccccag agctggcgga        60 agctggaccc agagccccac tggtggccct ttccctgggc cgggtc atg cgt tgc        115
                                                  Met Arg Cys
                                                    1 cgc aag tgc cag ctc tgc ctg tca gca ctg ctc aca ctc ctg ggc ctc       163
Arg Lys Cys Gln Leu Cys Leu Ser Ala Leu Leu Thr Leu Leu Gly Leu
  5                  10                  15 aaa gta tac atc gag tgg aca tcc gag tcc tgg ctt aaa aag gct gaa       211
Lys Val Tyr Ile Glu Trp Thr Ser Glu Ser Trp Leu Lys Lys Ala Glu
 20                  25                  30                  35 ccc cgg ggc gct ctg ccc agt ccc aca cca ccc aat gct gag ccc act       259
Pro Arg Gly Ala Leu Pro Ser Pro Thr Pro Pro Asn Ala Glu Pro Thr
                 40                  45                  50 ctg ccc acc aac ctc tca gca cgc ctg ggt cag act ggc cca ctg tcc       307
Leu Pro Thr Asn Leu Ser Ala Arg Leu Gly Gln Thr Gly Pro Leu Ser
             55                  60                  65 tct gct tac tgg aac cag cag cag cgg cag ctg gga gtc ctg ccc agt       355
Ser Ala Tyr Trp Asn Gln Gln Gln Arg Gln Leu Gly Val Leu Pro Ser
         70                  75                  80 acg gac tgt cag act tgg ggg act gtt gct gcc tcg gag atc ttg gac       403
```

```
Thr Asp Cys Gln Thr Trp Gly Thr Val Ala Ala Ser Glu Ile Leu Asp
 85                  90                  95 ttc atc ctg tac ccc cag gag ctt cgg cgc ttc ttg ctg tcg gcg gcc     451
Phe Ile Leu Tyr Pro Gln Glu Leu Arg Arg Phe Leu Leu Ser Ala Ala
100                 105                 110                 115 tgt agg agc ttt cca cta tgg ctg cct gca gga gaa ggc agc cct gtg     499
Cys Arg Ser Phe Pro Leu Trp Leu Pro Ala Gly Glu Gly Ser Pro Val
                120                 125                 130 gcc agc tgc tct gat aag gat gta ccc tac ttg cta ctg gct gtc aaa     547
Ala Ser Cys Ser Asp Lys Asp Val Pro Tyr Leu Leu Leu Ala Val Lys
                135                 140                 145 tca gaa cca gga cac ttt gca gca cgg cag gct gtg agg gag acc tgg     595
Ser Glu Pro Gly His Phe Ala Ala Arg Gln Ala Val Arg Glu Thr Trp
            150                 155                 160 ggc agc cca gtt gct ggg acc cgg ttg ctc ttc ctg ctg ggg tcc ccc     643
Gly Ser Pro Val Ala Gly Thr Arg Leu Leu Phe Leu Leu Gly Ser Pro
            165                 170                 175 cta gga atg ggg ggg cct gac tta aga tca ctg gtg acg tgg gaa agc     691
Leu Gly Met Gly Gly Pro Asp Leu Arg Ser Leu Val Thr Trp Glu Ser
180                 185                 190                 195 cgg cgc tat ggt gac cta ctg ctc tgg gac ttc ctg gat gtt ccc tac     739
Arg Arg Tyr Gly Asp Leu Leu Leu Trp Asp Phe Leu Asp Val Pro Tyr
                200                 205                 210 aac cgg aca ctc aag gac ctg ctg ctg acc tgg ctg agc cac cac         787
Asn Arg Thr Leu Lys Asp Leu Leu Leu Thr Trp Leu Ser His His
                215                 220                 225 tgc ccc gat gtc aat ttt gtc ctg cag gtt cag gat gat gcc ttt gtg     835
Cys Pro Asp Val Asn Phe Val Leu Gln Val Gln Asp Asp Ala Phe Val
                230                 235                 240 cac atc cca gcc cta ctg gag cac ctg cag act ctg cca ccc acc tgg     883
His Ile Pro Ala Leu Leu Glu His Leu Gln Thr Leu Pro Pro Thr Trp
            245                 250                 255 gcc cgc agc ctc tac ctg ggt gag atc ttc acc cag gcc aaa ccg ctc     931
Ala Arg Ser Leu Tyr Leu Gly Glu Ile Phe Thr Gln Ala Lys Pro Leu
260                 265                 270                 275 cgc aag ccc gga gga ccc ttc tat gtg ccg aag acc ttc ttt gaa ggg     979
Arg Lys Pro Gly Gly Pro Phe Tyr Val Pro Lys Thr Phe Phe Glu Gly
                280                 285                 290 gac tat cca gcc tat gcg agt gga ggt ggc tat gta atc tca gga cgc    1027
Asp Tyr Pro Ala Tyr Ala Ser Gly Gly Gly Tyr Val Ile Ser Gly Arg
                295                 300                 305 ctg gca ccc tgg ctg ctg cag gcg gca gct cgc gtg gca ccc ttc ccc    1075
Leu Ala Pro Trp Leu Leu Gln Ala Ala Ala Arg Val Ala Pro Phe Pro
                310                 315                 320 ttt gat gat gtc tac act ggc ttc tgc ttc cgt gcc ctg ggc tta gca    1123
Phe Asp Asp Val Tyr Thr Gly Phe Cys Phe Arg Ala Leu Gly Leu Ala
325                 330                 335 ccc cgt gcc cat cca ggc ttc ctc aca gcc tgg cca gca gaa cgt acc    1171
Pro Arg Ala His Pro Gly Phe Leu Thr Ala Trp Pro Ala Glu Arg Thr
340                 345                 350                 355 agg gac ccc tgc gcc gtg cga ggc ctg ctc ttg gtg cat cca gtc agc    1219
Arg Asp Pro Cys Ala Val Arg Gly Leu Leu Leu Val His Pro Val Ser
                360                 365                 370 cct cag gac acc att tgg ctc tgg aga cat ctg tgg gtc cca gag ctc    1267
Pro Gln Asp Thr Ile Trp Leu Trp Arg His Leu Trp Val Pro Glu Leu
                375                 380                 385 cag tgc tgaccggcag agacaagctg gggtgggtgg gtgctgacct ggcctgagtc    1323
Gln Cys tctcctagag acaagctggg gtgggtgggg ctgacctggc tgagtctct cctaaaccct    1383
```

```
tcctagccaa ggtggcagac tgtgtttatc tactttatgg ttttgaaaaa tgtgtccttc    1443
cta                                                                   1446
```

<210> SEQ ID NO 13
<211> LENGTH: 389
<212> TYPE: PRT
<213> ORGANISM: Mus musculus

<400> SEQUENCE: 13

```
Met Arg Cys Arg Lys Cys Gln Leu Cys Leu Ser Ala Leu Leu Thr Leu
 1               5                  10                  15

Leu Gly Leu Lys Val Tyr Ile Glu Trp Thr Ser Glu Ser Trp Leu Lys
             20                  25                  30

Lys Ala Glu Pro Arg Gly Ala Leu Pro Ser Pro Thr Pro Pro Asn Ala
         35                  40                  45

Glu Pro Thr Leu Pro Thr Asn Leu Ser Ala Arg Leu Gly Gln Thr Gly
     50                  55                  60

Pro Leu Ser Ser Ala Tyr Trp Asn Gln Gln Gln Arg Gln Leu Gly Val
 65                  70                  75                  80

Leu Pro Ser Thr Asp Cys Gln Thr Trp Gly Thr Val Ala Ala Ser Glu
                 85                  90                  95

Ile Leu Asp Phe Ile Leu Tyr Pro Gln Glu Leu Arg Arg Phe Leu Leu
            100                 105                 110

Ser Ala Ala Cys Arg Ser Phe Pro Leu Trp Leu Pro Ala Gly Glu Gly
        115                 120                 125

Ser Pro Val Ala Ser Cys Ser Asp Lys Asp Val Pro Tyr Leu Leu Leu
    130                 135                 140

Ala Val Lys Ser Glu Pro Gly His Phe Ala Ala Arg Gln Ala Val Arg
145                 150                 155                 160

Glu Thr Trp Gly Ser Pro Val Ala Gly Thr Arg Leu Leu Phe Leu Leu
                165                 170                 175

Gly Ser Pro Leu Gly Met Gly Gly Pro Asp Leu Arg Ser Leu Val Thr
            180                 185                 190

Trp Glu Ser Arg Arg Tyr Gly Asp Leu Leu Trp Asp Phe Leu Asp
        195                 200                 205

Val Pro Tyr Asn Arg Thr Leu Lys Asp Leu Leu Leu Thr Trp Leu
    210                 215                 220

Ser His His Cys Pro Asp Val Asn Phe Val Leu Gln Val Gln Asp Asp
225                 230                 235                 240

Ala Phe Val His Ile Pro Ala Leu Leu Glu His Leu Gln Thr Leu Pro
                245                 250                 255

Pro Thr Trp Ala Arg Ser Leu Tyr Leu Gly Glu Ile Phe Thr Gln Ala
            260                 265                 270

Lys Pro Leu Arg Lys Pro Gly Pro Phe Tyr Val Pro Lys Thr Phe
        275                 280                 285

Phe Glu Gly Asp Tyr Pro Ala Tyr Ala Ser Gly Gly Gly Tyr Val Ile
    290                 295                 300

Ser Gly Arg Leu Ala Pro Trp Leu Leu Gln Ala Ala Arg Val Ala
305                 310                 315                 320

Pro Phe Pro Phe Asp Asp Val Tyr Thr Gly Phe Cys Phe Arg Ala Leu
                325                 330                 335

Gly Leu Ala Pro Arg Ala His Pro Gly Phe Leu Thr Ala Trp Pro Ala
            340                 345                 350
```

-continued

```
Glu Arg Thr Arg Asp Pro Cys Ala Val Arg Gly Leu Leu Leu Val His
        355                 360                 365

Pro Val Ser Pro Gln Asp Thr Ile Trp Leu Trp Arg His Leu Trp Val
    370                 375                 380

Pro Glu Leu Gln Cys
385
```

<210> SEQ ID NO 14
<211> LENGTH: 1167
<212> TYPE: DNA
<213> ORGANISM: Artificial Sequence
<220> FEATURE:
<223> OTHER INFORMATION: degenerate sequence
<220> FEATURE:
<221> NAME/KEY: misc_feature
<222> LOCATION: (1)...(1167)
<223> OTHER INFORMATION: n = A,T,C or G

<400> SEQUENCE: 14

```
atgmgntgym gnaartgyca rytntgyytn wsngcnytny tnacnytnyt nggnytnaar     60
gtntayathg artggacnws ngarwsntgg ytnaaraarg cngarccnmg nggngcnytn    120
ccnwsnccna cnccnccnaa ygcngarccn acnytnccna cnaayytnws ngcnmgnytn    180
ggncaracng gnccnytnws nwsngcntay tggaaycarc arcarmgnca rytnggngtn    240
ytnccnwsna cngaytgyca racntggggn acngtngcng cnwsngarat hytngaytty    300
athytntayc cncargaryt nmgnmgntty ytnytnwsng cngcntgymg nwsnttyccn    360
ytntggytnc cngcnggnga rggnwsnccn gtngcnwsnt gywsngayaa rgaygtnccn    420
tayytnytny tngcngtnaa rwsngarccn ggncayttyg cngcnmgnca rgcngtnmgn    480
garacntggg gnwsnccngt ngcnggnacn mgnytnytnt tyytnytngg nwsnccnytn    540
ggnatgggng gnccngayyt nmgnwsnytn gtnacntggg arwsnmgnmg ntayggngay    600
ytnytnytnt gggayttyyt ngaygtnccn tayaaymgna cnytnaarga yytnytnytn    660
ytnacntggy tnwsncayca ytgyccngay gtnaayttyg tnytncargt ncargaygay    720
gcnttygtnc ayathccngc nytnytngar cayytncara cnytnccncc nacntgggcn    780
mgnwsnytnt ayytnggnga rathttyacn cargcnaarc cnytnmgnaa rccnggnggn    840
ccnttytayg tnccnaarac nttyttygar ggngaytayc cngcntaygc nwsnggnggn    900
ggntaygtna thwsnggnmg nytngcnccn tggytnytnc argcngcngc nmgngtngcn    960
ccnttyccnt tygaygaygt ntayacnggn ttytgyttym gngcnytngg nytngcnccn   1020
mgngcncayc cnggnttyyt nacngcntgg ccngcngarm gnacnmgnga yccntgygcn   1080
gtnmgnggny tnytnytngt ncayccngtn wsnccncarg ayacnathtg gytntggmgn   1140
cayytntggg tnccngaryt ncartgy                                        1167
```

<210> SEQ ID NO 15
<211> LENGTH: 35
<212> TYPE: DNA
<213> ORGANISM: Artificial Sequence
<220> FEATURE:
<223> OTHER INFORMATION: oligonucleotide ZC20336

<400> SEQUENCE: 15

```
gcgagcgttt aaacgccacc atgcgctgcc ccaag                                35
```

<210> SEQ ID NO 16
<211> LENGTH: 32
<212> TYPE: DNA

```
<213> ORGANISM: Artificial Sequence
<220> FEATURE:
<223> OTHER INFORMATION: oligonucleotide ZC20316

<400> SEQUENCE: 16
cgtatcggcg cgcctcagca ctggagcctt gg                                32

<210> SEQ ID NO 17
<211> LENGTH: 18
<212> TYPE: DNA
<213> ORGANISM: Artificial Sequence
<220> FEATURE:
<223> OTHER INFORMATION: Oligonucleotide primer, 19140

<400> SEQUENCE: 17
gtgcccgagt ccttcttc                                                18

<210> SEQ ID NO 18
<211> LENGTH: 18
<212> TYPE: DNA
<213> ORGANISM: Artificial Sequence
<220> FEATURE:
<223> OTHER INFORMATION: oligonucleotide primer, ZC19141

<400> SEQUENCE: 18
gcaaaggcca gtgtagac                                                18

<210> SEQ ID NO 19
<211> LENGTH: 43
<212> TYPE: DNA
<213> ORGANISM: Artificial Sequence
<220> FEATURE:
<223> OTHER INFORMATION: Oligonucleotide, ZC25177

<400> SEQUENCE: 19
atgcattaac cctcactaaa gggcatgcct ctccggaagc cag                    43

<210> SEQ ID NO 20
<211> LENGTH: 43
<212> TYPE: DNA
<213> ORGANISM: Artificial Sequence
<220> FEATURE:
<223> OTHER INFORMATION: Oligonucleotide, ZC25232

<400> SEQUENCE: 20
taatacgact cactataggg aggcaaaaac agtccaccac ccc                    43
```

BETA-1,3-GALACTOSYLTRANSFERASE HOMOLOGS

REFERENCE TO RELATED APPLICATIONS

This application is related to Provisional Application No. 60/111,697 filed on Dec. 10, 1998. Under 35 U.S.C. §119 (e)(1), this application claims benefit of said Provisional Application.

BACKGROUND OF THE INVENTION

Beta-1,3-galactosyltransferase molecules are classified in the family of glycosyltransferases. In addition to transferring carbohydrate molecules to glycoproteins during biosynthesis, members of this family have also been detected on the cell surface where they are thought to be involved in varying aspects of cell-cell interactions. This family includes carbohydrate transferring enzymes, such as sialyltransferases and fucosyltransferases, and galactosyltransferases. During the formation of O-linked glycoproteins and the modification of N-linked ones, each sugar transfer is catalyzed by a different type of glycosyltransferase. Each glycosyltransferase enzyme is specific for both the donor sugar nucleotide and the acceptor molecule.

Galactosyltransferases promote the transfer of an activated galactose residue in UDP-galactose to the monosaccharide N-acetylglucosamine. This transfer is a step in the biosynthesis of the carbohydrate portion of galactose-containing glycoproteins, such as oligosaccharides and glycolipids, in animal tissues. The Beta-1,3-galactosyltransferases are characterized by the elongation of type I oligosaccharide chains, and the Beta-1,4-galactosyltransferases are characterized by the elongation of type II oligosaccharide chains. Both types of carbohydrate structures are present in soluble oligosaccharides of human milk, and are also found on glycoproteins and glycolipids, and are important precursors of blood group antigens. Both galactosyltransferases require a divalent cation ($Mn^{2+}$) to function. Beta-1,4-galactosyltransferases are expressed in various cell types and tissues, while the Beta-1,3-galactosyltransferases seem to have more restricted tissue distributions.

Some galactosyltransferases are found in the Golgi apparatus. These Golgi-localized enzymes have structure similarity: a short N-terminal domain that faces the cytosol, a single transmembrane α helix, and a large C-terminal domain that faces the Golgi lumen and that contains the catalytic site. The transmembrane α helix is necessary and sufficient to restrict the enzyme to the Golgi. Of the Beta-1,3-galactosyltransferase family two members (See Amado, M. et al., *J. Biol. Chem.* 273, 21: 12770–12778, 1998) have been predicted to have two potentially different initiation codons, resulting in two different N-terminal cytoplasmic domains.

Additionally, galactosyltransferases have been shown to be expressed on the cell surface, where their function is theorized to participate in cellular interactions, perhaps as receptors, or receptor-like complementary molecules. As a cell surface carbohydrate, galactosyltransferases have been implicated in varied biology such as cell migration, contact inhibition, tissue interactions, neuronal specificity, fertilization, embryonic cell adhesions, limb bud morphogenesis, mesenchyme development, immune recognition, growth control, and tumor metastasis. See, for example, Shur, B. D., *Mol Cell Bioc.* 61:143–158, 1984.

The failure of tumor cell-tumor cell adhesion is believed to be a contributing factor to tumor metastases. See, for example, Zetter, *Cancer Biology*, 4: 219–29, 1993. Metastases, in turn, are generally associated with poor prognosis for cancer treatment. The metastatic process involves a variety of cellular events, including angiogenesis, tumor cell invasion of the vascular or lymphatic circulation, tumor cell arrest at a secondary site; tumor cell passage across the vessel wall into the parenchymal tissue, and tumor cell proliferation at the secondary site. Thus, both positive and negative regulation of adhesion are necessary for metastasis. That is, tumor cells must break away from the primary tumor mass, travel in circulation and adhere to cellular and/or extracellular matrix elements at a secondary site. Molecules capable of modulating cell-cell and cell-matrix adhesion are therefore sought for the study, diagnosis, prevention or treatment of metastases.

β1→3 Galactosyltransferases have limited homology to each other. In contrast to other glycosyltransferases, they do not appear to be localized to the same chromosomes. Additionally, a member of this family has recently been identified in Drosophila. This molecule, Brainiac, is involved in contact and adhesion between germ-line and follicle cells (Amado, M. et al., *J. Biol. Chem.* 273, 21: 12770–12778, 1998).

A deficiency of Beta-1,3-galactosyltransferase enzymes has been noticed in the Tn-syndrome. This syndrome is a rarely acquired disorder affecting all hemopoietic lineages, and is characterized by the expression of the Tn and the sialosyl-Tn antigens on the cell surface. The Tn is αN-acetylgalactosamine linked O-glycosidically to threonine or serine residues of membrane proteins. These antigens bind naturally occurring serum antibodies thereby leading to mild hemolytic anemia and pronounced thrombopenia. Thus, the blood cells in the Tn-syndrome are expected to carry less sialic acid if galactose can not be transferred to N-Acetylgalactosamine. The expression of Tn and sialosyl-Tn antigens as a consequence of imcomplete or disordered gylcan biosynthesis has been recognized as a cancer-associated phenomenon. Tn and sialosyl-Tn antigens are among the most investigated cancer-associated carbohydrates antigens.

The present invention provides such polypeptides for these and other uses that should be apparent to those skilled in the art from the teachings herein.

SUMMARY OF THE INVENTION

Within one aspect, the present invention provides an isolated polypeptide comprising residues 148 to 397 of SEQ ID NO:2. Within an embodiment, the isolated polypeptide comprises residues 19 to 397 of SEQ ID NO:2. Within another embodiment, the isolated polypeptide comprises residues 1 to 397 of SEQ ID NO:2.

Within another aspect, the present invention provides an isolated polypeptide selected from the group consisting of: a polypeptide comprising residues 1 to 18 of SEQ ID NO:2; a polypeptide comprising residues 19 to 147 of SEQ ID NO:2; a polypeptide comprising residues 148 to 397 of SEQ ID NO:2; a polypeptide comprising residues 19 to 397 of SEQ ID NO:2; and a polypeptide comprising residues 1 to 397 of SEQ ID NO:2.

Within another aspect, the present invention provides an isolated polynucleotide encoding a polypeptide wherein the polypeptide comprises residues 148 to 397 of SEQ ID NO:2. Within an embodiment, the polypeptide molecule comprises residues 19 to 397 of SEQ ID NO:2. Within another embodiment, the polypeptide molecule comprises residues 1 to 397 of SEQ ID NO:2.

Within another aspect, the present invention provides an isolated polynucleotide encoding a polypeptide molecule wherein the polypeptide is selected from the group consisting of: a polypeptide comprising residues 1 to 18 of SEQ ID NO:2; a polypeptide comprising residues 19 to 147 of SEQ ID NO:2; a polypeptide comprising residues 148 to 397 of SEQ ID NO:2; a polypeptide comprising residues 19 to 397 of SEQ ID NO:2; and a polypeptide comprising residues 1 to 397 of SEQ ID NO:2. Within an embodiment is provided an expression vector comprising the following operably linked elements: a) a transcription promoter; b) a DNA segment wherein the DNA segment is a polynucleotide encoding the polypeptide of claim 1; and a transcription terminator. Within another embodiment the DNA segment contains an affinity tag. Within another embodiment, the invention provides a cultured cell into which has been introduced the expression vector, wherein said cell expresses the polypeptide encoded by the DNA segment. Within another embodiment the invention provides a method of producing a polypeptide comprising culturing the cell, whereby said cell expresses the polypeptide encoded by the DNA segment; and recovering the polypeptide.

Within another aspect is provided a method of producing an antibody comprising the following steps in order: inoculating an animal with a polypeptide selected from the group consisting of: a polypeptide comprising residues 1 to 18 of SEQ ID NO:2; a polypeptide comprising residues 19 to 147 of SEQ ID NO:2; a polypeptide comprising residues 148 to 397 of SEQ ID NO:2; a polypeptide comprising residues 19 to 397 of SEQ ID NO:2; and a polypeptide comprising residues 1 to 397 of SEQ ID NO:2, wherein the polypeptide elicits an immune response in the animal to produce the antibody; and isolating the antibody from the animal. Within an embodiment the antibody produced binds to a residues 1 to 397 of SEQ ID NO:2. Within another embodiment the antibody is a monoclonal antibody. Within another embodiment the antibody specifically binds to a polypeptide of residues 1 to 397 of SEQ ID NO:2.

Within another aspect is provided a method of producing an antibody comprising the following steps in order: inoculating an animal with an epitope bearing portion of a polypeptide wherein the epitope bearing portion is selected from the group consisting of: a polypeptide consisting of residues 1 to 6 of SEQ ID NO:2; a polypeptide consisting of residues 26 to 54 of SEQ ID NO:2; a polypeptide consisting of residues 82 to 94 of SEQ ID NO:2; a polypeptide consisting of residues 110 to 117 of SEQ ID NO:2; a polypeptide consisting of residues 110 to 127 of SEQ ID NO:2; a polypeptide consisting of residues 122 to 127 of SEQ ID NO:2; a polypeptide consisting of residues 122 to 136 of SEQ ID NO:2; a polypeptide consisting of residues 131 to 136 of SEQ ID NO:2; a polypeptide consisting of residues 131 to 146 of SEQ ID NO:2; a polypeptide consisting of residues 139 to 146 of SEQ ID NO:2; a polypeptide consisting of residues 154 to 177 of SEQ ID NO:2; a polypeptide consisting of residues 187 to 197 of SEQ ID NO:2; a polypeptide consisting of residues 187 to 207 of SEQ ID NO:2; a polypeptide consisting of residues 202 to 207 of SEQ ID NO:2; a polypeptide consisting of residues 282 to 289 of SEQ ID NO:2; a polypeptide consisting of residues 282 to 301 of SEQ ID NO:2; a polypeptide consisting of residues 295 to 301 of SEQ ID NO:2; a polypeptide consisting of residues 358 to 365 of SEQ ID NO:2; a polypeptide consisting of residues 358 to 397 of SEQ ID NO:2; and a polypeptide consisting of residues 387 to 397 of SEQ ID NO:2; wherein the polypeptide elicits an immune response in the animal to produce the antibody; and isolating the antibody from the animal. Within an embodiment the antibody which binds to a residues 1 to 397 of SEQ ID NO:2. Within another embodiment, the antibody is a monoclonal antibody.

Within another aspect the invention provides a method for modulating cell-cell interactions by combining the polypeptide of residues 148 to 397, with cells in vivo and in vitro. Within an embodiment the cells are derived from tissues selected from the group consisting of: a) tissues from pancreas; b) tissues from colon; c) tissues from small intestine; d) tissues from bladder; e) tissues from prostate; f) tissues from myometrium; and g) tissues from breast.

Within another aspect the invention provides a method for modulating glycoprotein and glycolipid biosynthesis by combining the polypeptide according to claim 1, with cells in vivo and in vitro. Within an embodiment the cells are derived from tissues selected from the group consisting of: a) tissues from pancreas; b) tissues from colon; c) tissues from small intestine; d) tissues from bladder; e) tissues from prostate; f) tissues from myometrium; and g) tissues from breast.

Within another aspect, the invention provides a method of detecting a molecule which binds to a polypeptide comprising contacting the polypeptide with a test sample containing the molecule wherein the polypeptide comprises residues 148 to 397 of SEQ ID NO:2 and whereby the molecule binds the polypeptide.

These and other aspects of the invention will become evident upon reference to the following detailed description of the invention and attached drawings.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–1210, 1988), streptavidin binding peptide, maltose binding protein (Guan et al., *Gene* 67:21–30, 1987), cellulose binding protein, thioredoxin, ubiquitin, T7 polymerase, or other antigenic epitope or binding domain. See, in general, Ford et al., *Protein Expression and Purification* 2: 95–107, 1991. DNAs encoding affinity tags and other reagents are available from commercial suppliers (e.g., Pharmacia Biotech, Piscataway, N.J.; New England Biolabs, Beverly, Mass.; Eastman Kodak, New Haven, Conn.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGAGCTT-3' are 5'-AGCTTgagt-3' and 3'-tcgacTACC-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function (s) of the sequences are retained.

The term "ortholog" or "species homolog", denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, a-globin, b-globin, and myo-globin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain or multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based upon the discovery of a novel cDNA sequence (SEQ ID NO:1) and corresponding polypeptide (SEQ ID NO:2) having homology to a family of proteins, the β1→3galactosyltransferases (β1→3GalTases). β1→3GalTases are the β3 subfamily of human galactosyltransferases β3Gal-T family) which includes HSY15014 (Kolbinger, F. et al., *Journal of Biol. Chem.* 273: 433–440, 1998), HSGALT3, HSGALT4, (Amado, M. et al., ibid) and E07739 (Katsutoshi, S. et al., Japanese patent, JP 1994181759-A/1). β1→3GalTases are responsible for transferring galactose to carbohydrate chains during biosynthesis.

It has been predicted that β1→3GalTases are in the alpha/beta barrel (TIM barrel) folding class of enzymes, similar to other glycosyltransferases such as the alpha-amylases and beta-glycanases (Yuan, Y. et al., *Cell* 88:9–11, 1997). Also in the β3Gal-T family is the *Drosophila melanogaster* Brainiac, (BRN) (Goode, S. et al., *Devel. Biol.* 178:35–50, 1996), known as "putative neurogenic secreted signaling protein" or NSSP. BRN is required for epithelial development. This activity may be due to possible cell interactions between the membrane bound glycosyltransferase and oligosaccharide substrates on adjacent cell surfaces (Shur, ibid). Thus, β3Gal-T family members are also known as neurogenic secreted signal peptides. See, for example, Shur, B. D., ibid, and Amado, M. et al., ibid. This novel polypeptide and its polynucleotides have been designated znssp2.

The β3Gal-Ts are predicted to be Type II transmembrane proteins. An ortholog to E07739, is AF029790 (Hennet, T. et al., *Journal of Biol. Chem.* 273:58–65, 1998), which is claimed to be a Type II transmembrane domain based on hydrophobicity analysis. However, due to the close proximity of this domain to the initiating methionine and lack of positively charged residues preceding the domain it is possible that AF029790 is not membrane bound but rather a extracellular secreted protein.

The novel znssp2 polypeptide-encoding polynucleotides of the present invention were initially identified by searching an EST database for open reading frames with similarity to BRN. The insert of an expressed sequence tag corresponding to nucleotides 673 to 1532 of SEQ ID NO:1 was used to obtain a clone that had been isolated from a bone marrow library. Analysis of the DNA encoding a znssp2 polypeptide (SEQ ID NO:1) revealed an open reading frame encoding 397 amino acids (SEQ ID NO: 2). Znssp2 shares homology with β3Gal-T's which are predicted to be Type II membrane proteins. Znssp2 shows the highest similarity to HSGALT3, at 34% amino acid identity over the region of amino acids from residue 148 to residue 348 of SEQ ID NO:2. Amino acid residues 19 to 147 of SEQ ID NO:2 are predicted to form a "stem" domain, and amino acid residues 148 to 397 of SEQ ID NO:2 are predicted to form a "catalytic" domain.

Due to the close proximity of the hydrophobic domain (residues 1 to 18 of SEQ ID NO:2) to the initiation methionine, and the lack of positively charged residues preceding this domain, it is possible that znssp2 is a secreted protein comprising a signal peptide of 18 amino acid residues (residues 1–18 of SEQ ID NO:2) and a mature polypeptide of 379 amino acids (residues 19 to 397 of SEQ ID NO:2). Conserved negatively charged amino acid residues 202, 208, 216, 248, 333, and 334 of SEQ ID NO:2 are contained within the catalytic domain. Additionally, the sequence of amino acid residues from residue 333 to 338 is representative of a peptide motif of this family. This motif is further described by the following amino acid residue profile: [D,E][D][V][F,Y][L,T,V][G]. Those skilled in the art will recognize that predicted domain boundaries are approximations based on primary sequence content, and may vary slightly; however, such estimates are generally accurate to within ±5 amino acid residues.

The present invention also provides post translationally modified polypeptides or polypeptide fragments. A potential N-linked glycosylation site can be found at amino acid residue 220 of SEQ ID NO:2. Post translational modifications in members of the β3Gal-T family may regulate whether the protein is expressed in the Golgi or on the surface of the cell. Other examples of post translational modifications include proteolytic cleavage, disulfide bonding and hydroxylation.

Additionally, znssp2 has 29% homology to the BRN gene.

The present invention also includes the murine ortholog of znssp2 (znssp2-m) which was identified in a mouse EST database. The polynucleotide, polypeptide, and degenerate sequences of znssp2-m are shown in SEQ ID NOs:12, 13, and 14, respectively.

Analysis of the tissue distribution of znssp2 was performed by the Northern blotting technique using Human Multiple Tissue and Master Dot Blots. A very strong signal of 1.2 kb was seen in pancreas. A strong signal was seen in colon; with less strong signals seen in spinal cord, bone marrow, small intestine, and peripheral blood leukocytes. Fainter signals were seen in heart, lung, spleen, prostate, stomach, thyroid, trachea, placenta, skeletal muscle, kidney and lymph node.

The highly conserved, negatively charged residues at positions 202, 208, 216, 248, 333, and 334 of SEQ ID NO:2 and the amino acid sequence between 333 and 338 of znssp2 can be used as a tool to identify new family members. For instance, reverse transcription-polymerase chain reaction (RT-PCR) can be used to amplify sequences encoding the znssp2 polynucleotide from RNA obtained from a variety of tissue sources or cell lines. In particular, highly degenerate primers designed from the znssp2 sequences are useful for this purpose.

The present invention further provides polynucleotide molecules, including DNA and RNA molecules, encoding znssp2 proteins. The polynucleotides of the present invention include the sense strand; the anti-sense strand; and the DNA as double-stranded, having both the sense and anti-sense strand annealed together by their respective hydrogen bonds. Representative DNA sequences encoding znssp2 proteins are set forth in SEQ ID NOs:1, 3, 12 and 14. DNA sequences encoding other znssp2 proteins can be readily generated by those of ordinary skill in the art based on the genetic code.

The present invention also provides polynucleotide molecules, including DNA and RNA molecules, that encode the znssp2 polypeptides disclosed herein. Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the znssp2 polypeptide of SEQ ID NO:2. SEQ ID NO:14 is a degenerate DNA sequence that encompasses all DNAs that encode the znssp2 polypeptide of SEQ ID NO:13. Those skilled in the art will recognize that the degenerate sequence of SEQ ID NO:3 also provides all RNA sequences encoding SEQ ID NO:2 by substituting U for T and in the same manner, all the degenerate sequences of SEQ ID NO:14 also provides all RNA sequences encoding SEQ ID NO:13. Thus, znssp2 polypeptide-encoding polynucleotides comprising nucleotide 1 to nucleotide 1191 of SEQ ID NO:3 and their RNA equivalents, and the polypeptide-encoding polynucleotides comprising nucleotide 1 to nucleotide 1167 of SEQ ID NO:14 are contemplated by the present invention. Table 1 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOs:3 and 14, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B |  | RAY |
| Glu\|Gln | Z |  | SAR |
| Any | X |  | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NOs:2 or 13. Variant sequences can be readily tested for functionality as described herein.

One of ordinary skill in the art will also appreciate that different species can exhibit "preferential codon usage." In general, see, Grantham, et al., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, *Gene*

18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed in SEQ ID NOs:3 and 14 serve as a templates for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NOs:1 or 12, other polynucleotide probes, primers, fragments and sequences recited herein or sequences complementary thereto. Polynucleotide hybridization is well known in the art and widely used for many applications, see for example, Sambrook et al., *Molecular Cloning: A Laboratory Manual, Second Edition,* Cold Spring Harbor, N.Y., 1989; Ausubel et al., eds., *Current Protocols in Molecular Biology,* John Wiley and Sons, Inc., NY, 1987; Berger and Kimmel, eds., Guide to Molecular Cloning Techniques, *Methods in Enzymology,* volume 152, 1987 and Wetmur, *Crit. Rev. Biochem. Mol. Biol.* 26:227–59, 1990. Polynucleotide hybridization exploits the ability of single stranded complementary sequences to form a double helix hybrid. Such hybrids include DNA-DNA, RNA-RNA and DNA-RNA.

Hybridization will occur between sequences which contain some degree of complementarity. Hybrids can tolerate mismatched base pairs in the double helix, but the stability of the hybrid is influenced by the degree of mismatch. The $T_m$ of the mismatched hybrid decreases by 1° C. for every 1–1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Hybridization buffers generally contain blocking agents such as Denhardt's solution (Sigma Chemical Co., St. Louis, Mo.), denatured salmon sperm DNA, milk powders (BLOTTO), heparin or SDS, and a $Na^+$ source, such as SSC (1×SSC: 0.15 M NaCl, 15 mM sodium citrate) or SSPE (1×SSPE: 1.8 M NaCl, 10 mM $NaH_2PO_4$, 1 mM EDTA, pH 7.7). By decreasing the ionic concentration of the buffer, the stability of the hybrid is increased. Typically, hybridization buffers contain from between 10 mM to 1 M $Na^+$. Premixed hybridization solutions are also available from commercial sources such as Clontech Laboratories (Palo Alto, Calif.) and Promega Corporation (Madison, Wis.) for use according to manufacturer's instruction. Addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

Stringent hybridization conditions encompass temperatures of about 5–25° C. below the thermal melting point ($T_m$) of the hybrid and a hybridization buffer having up to 1 M $Na^+$. Higher degrees of stringency at lower temperatures can be achieved with the addition of formamide which reduces the $T_m$ of the hybrid about 1° C. for each 1% formamide in the buffer solution. Generally, such stringent conditions include temperatures of 20–70° C. and a hybridization buffer containing 5× to 6×SSC and 0–50% formamide. A higher degree of stringency can be achieved at temperatures of from 40–70° C. with a hybridization buffer having 3× to 4×SSC and from 0–50% formamide. Highly stringent conditions typically encompass temperatures of 42–70° C. with a hybridization buffer having up to 2×SSC and 0–50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions that influence the $T_m$ include, the size and base pair content of the polynucleotide probe, the ionic strength of the hybridization solution, and the presence of destabilizing agents in the hybridization solution. Numerous equations for calculating $T_m$ are known in the art, see for example (Sambrook et al., ibid.; Ausubel et al., ibid.; Berger and Kimmel, ibid. and Wetmur, ibid.) and are specific for DNA, RNA and DNA-RNA hybrids and polynucleotide probe sequences of varying length. Sequence analysis software such as Oligo 4.0 and Primer Premier, as well as sites on the Internet, are available tools for analyzing a given sequence and calculating $T_m$ based on user defined criteria. Such programs can also analyze a given sequence under defined conditions and suggest suitable probe sequences. Typically, hybridization of longer polynucleotide sequences, >50 bp, is done at temperatures of about 20–25° C. below the calculated $T_m$. For smaller probes, <50 bp, hybridization is typically carried out at the $T_m$ or 5–10° C. below. This allows for the maximum rate of hybridization for DNA-DNA and DNA-RNA hybrids.

As previously noted, the isolated polynucleotides of the present invention include DNA and RNA. Methods for preparing DNA and RNA are well known in the art. In general, RNA is isolated from a tissue or cell that produces large amounts of znssp2 RNA. Such tissues and cells are identified by Northern blotting (Thomas, *Proc. Natl. Acad. Sci. USA* 77:5201, 1980), and include pancreas, colon, spinal cord, small intestine, heart, lung, spleen, kidney, prostate, peripheral blood leukocytes, stomach, thyroid, and trachea. Total RNA can be prepared using guanidine isothiocyante extraction followed by isolation by centrifugation in a CsCl gradient (Chirgwin et al., *Biochemistry* 18:52–94, 1979). Poly $(A)^+$ RNA is prepared from total RNA using the method of Aviv and Leder (*Proc. Natl. Acad. Sci. USA* 69:1408–12, 1972). Complementary DNA (cDNA) is prepared from poly$(A)^+$ RNA using known methods. In the alternative, genomic DNA can be isolated. Polynucleotides encoding znssp2 polypeptides are then identified and isolated by, for example, hybridization or PCR.

A full-length clone encoding znssp2 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to znssp2, or fragments thereof, or other specific binding partners.

The invention also provides isolated and purified znssp2 polynucleotide probes. Such polynucleotide probes can be RNA or DNA. DNA can be either cDNA or genomic DNA. Polynucleotide probes are single or double-stranded DNA or RNA, generally synthetic oligonucleotides, but may be generated from cloned cDNA or genomic sequences and will generally comprise at least 16 nucleotides, more often from 17 nucleotides to 25 or more nucleotides, sometimes 40 to 60 nucleotides, and in some instances a substantial portion, domain or even the entire znssp2 gene or cDNA. The synthetic oligonucleotides of the present invention have at least 75% identity to a representative znssp2 DNA sequence (SEQ ID NOs:1,3, 12 or 14) or their complements. The invention also provides oligonucleotide probes or primers comprising at least 14 contiguous nucleotides of a polynucleotide of SEQ ID NOs: 1,3,12, or 14 or a sequence complementary to SEQ ID NOs: 1,3, 12 or 14.

Regions from which to construct probes include the 5' and/or 3' coding sequences, substrate binding regions, and signal sequences, and the like. Techniques for developing polynucleotide probes and hybridization techniques are known in the art, see for example, Ausubel et al., eds., *Current Protocols in Molecular Biology,* John Wiley and Sons, Inc., NY, 1991. For use as probes, the molecules can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art. Such probes can also be used in hybridizations to detect the presence or quantify the amount of znssp2 gene or mRNA transcript in a sample. Znssp2 polynucleotide probes could be used to hybridize to DNA or RNA targets for diagnostic purposes, using such techniques such as fluorescent in situ hybridization (FISH) or immunohistochemistry. Polynucleotide probes can be used to identify genes encoding znssp2-like proteins. For example, znssp2 polynucleotides can be used as primers and/or templates in PCR reactions to identify other novel members of the UDP-glycosyltransferase family. Such probes can also be used to screen libraries for related sequences encoding novel UDP-glycosyltransferases. Such screening would be carried out under conditions of low stringency which would allow identification of sequences which are substantially homologous, but not requiring complete homology to the probe sequence. Such methods and conditions are well known in the art, see, for example, Sambrook et al., *Molecular Cloning: A Laboratory Manual,* Second Edition, Cold Spring Harbor, N.Y., 1989. Such low stringency conditions could include hybridization temperatures less than 42° C., formamide concentrations of less than 50% and moderate to low concentrations of salt. Libraries may be made of genomic DNA or cDNA. Polynucleotide probes are also useful for Southern, Northern, or dot blots, colony and plaque hybridization and in situ hybridization. Mixtures of different znssp2 polynucleotide probes can be prepared which would increase sensitivity or the detection of low copy number targets, in screening systems.

The polynucleotides of the present invention can also be synthesized using DNA synthesizers. Currently the method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. See Glick and Pasternak, *Molecular Biotechnology, Principles & Applications of Recombinant DNA,* (ASM Press, Washington, D.C. 1994); Itakura et al., *Annu. Rev. Biochem.* 53: 323–56, 1984 and Climie et al., *Proc. Natl. Acad. Sci. USA* 87:633–7, 1990.

The present invention further provides counterpart polypeptides and polynucleotides from other species (orthologs). These species include, but are not limited to mammalian, avian, amphibian, reptile, fish, insect and other vertebrate and invertebrate species. Of particular interest are znssp2 polypeptides from other mammalian species, including murine, porcine, ovine, bovine, canine, feline, equine, and other primate polypeptides. Orthologs of human znssp2 can be cloned using information and compositions provided by the present invention in combination with conventional cloning techniques. For example, a cDNA can be cloned using mRNA obtained from a tissue or cell type that expresses znssp2 as disclosed herein. Suitable sources of mRNA can be identified by probing Northern blots with probes designed from the sequences disclosed herein. A library is then prepared from mRNA of a positive tissue or cell line. A znssp2-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human znssp2 sequence disclosed herein. Within an additional method, the cDNA library can be used to transform or transfect host cells, and expression of the cDNA of interest can be detected with an antibody to znssp2 polypeptide. Similar techniques can also be applied to the isolation of genomic clones.

Those skilled in the art will recognize that the sequences disclosed in SEQ ID NOd:1, and 12 represent single alleles of human and mouse znssp2, respectively and that allelic variation and alternative splicing are expected to occur. Allelic variants of this sequence can be cloned by probing cDNA or genomic libraries from different individuals according to standard procedures. Allelic variants of the DNA sequence shown in SEQ ID NOs:1 and 12, including those containing silent mutations and those in which mutations result in amino acid sequence changes, are within the scope of the present invention, as are proteins which are allelic variants of SEQ ID NOs:2 and 13. cDNAs generated from alternatively spliced mRNAs, which retain the properties of the znssp2 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated znssp2 polypeptides that are substantially homologous to the polypeptides of SEQ ID NOs:2 and 12 and their orthologs. The term "substantially homologous" is used herein to denote polypeptides having 50%, preferably 60%, more preferably at least 80%, sequence identity to the sequences shown in SEQ ID NOs:2 and 13 or their orthologs. Such polypeptides will more preferably be at least 90% identical, and most preferably 95% or more identical to SEQ ID NOs:2 and 13 or their orthologs.) Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from four to six.

The present invention includes nucleic acid molecules that encode a polypeptide having one or more conservative

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant znssp2. The FASTA algorithm is described amino acid changes, compared with the amino acid sequences of SEQ ID NOs:2 and 13. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. As used herein, the language "conservative amino acid substitution" refers to a substitution represented by a BLOSUM62 value of greater than −1. For example, an amino acid substitution is conservative if the substitution is characterized by a BLOSUM62 value of 0, 1, 2, or 3. Conservative amino acid substitutions are characterized by a BLOSUM62 value of at least 1 (e.g, 1, 2 or 3), while more conservative amino acid substitutions are characterized by a BLOSUM62 value of at least 2 (e.g., 2 or 3).

Variant znssp2 polypeptides or substantially homologous znssp2 polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20–25 residues, or an affinity tag. The present invention thus includes polypeptides of from 397 to 410 amino acid residues that comprise a-sequence that is at least 70%, preferably at least 80%, and more preferably 90% or more identical to the corresponding region of SEQ ID NO:2. Polypeptides comprising affinity tags can further comprise a proteolytic cleavage site between the znssp2 polypeptide and the affinity tag. Preferred such sites include thrombin cleavage sites and factor Xa cleavage sites.

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention further provides a variety of other polypeptide fusions and related multimeric proteins comprising one or more polypeptide fusions. For example, a znssp2 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-znssp2 polypeptide fusions can be expressed in genetically engineered cells to produce a variety of multimeric znssp2 analogs. Auxiliary domains can be fused to znssp2 polypeptides to target them to specific cells, tissues, or macromolecules (e.g., pancreas, colon, spinal cord, bone marrow, heart, and small intestine etc.). For example, a protease, or ablation antibody polypeptide or protein could be targeted to a predetermined cell type by fusing a said protease, or ablation antibody polypeptide to a ligand that specifically binds to a receptor or receptor-like complementary molecule on the surface of the target cell, such as, pancreas, colon, spinal cord, or bone marrow. In this way, polypeptides and proteins can be targeted for therapeutic or diagnostic purposes. Such beta-1,3-galactosyltransferase polypeptides can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

Polypeptide fusions of the present invention will generally contain not more than about 1,700 amino acid residues, not more than about 1,200 residues, or not more than about 1,000 residues, and will in many cases be considerably smaller. For example, residues of znssp2 polypeptide can be fused to E, coli β-galactosidase (1,021 residues; see Casadaban et al., *J. Bacteriol.* 143:971–980, 1980), a 10-residue spacer, and a 4-residue factor Xa cleavage site. In a second example, residues of znssp2 polypeptide can be fused to maltose binding protein (approximately 370 residues), a 4-residue cleavage site, and a 6-residue polyhistidine tag.

Some proteins in the β3Gal-T family been shown to be expressed intracellulary and are involved in intracellular glycoprotein and glycolipid processing. Other members of this family have been shown to be extracellularly expressed and are involved in glycoprotein and glycolipid processing (such as in the case of the Tn antigen). Other members of the family are expressed extracellularly and are involved in cell-cell interactions and intracellular signaling. Thus, molecules of the present invention can function as an enzyme both intracellularly and extracellulary, in which case its anti-complementary molecule is a substrate. Additionally, molecules of the present invention can function extracellularly and modulate cell-cell interactions. The extracellular binding of znssp2 to its anti-complementary molecule can cause a cellular event in the cell that is expressing it (i.e. znssp2 acts as a receptor or receptor-like molecule), or in the cell expressing the anti-complementary molecule to which it binds (i.e., znssp2 acts as a ligand). Additionally, znssp2 can function extracellularly as a soluble enzyme, ligand, receptor or receptor like molecule. Similarly, as an extracellulary expressed znssp2 enzyme, the processing of its anti-complementary substrate can result in a cellular response (similar to intracellular signaling) in the cell expressing the substrate. Also as an extracellularly expressed protein, znssp2 can function to form a "bridge" between cells maintaining their proximity to each other. Thus, for the purposes of this application, znssp2 is referred to as a complementary molecule and its cognate binding partner is referred to as an anti-complementary molecule.

The invention also provides soluble znssp2 polypeptides, used to form fusion or chimeric proteins with human Ig, as His-tagged proteins, or FLAG™-tagged proteins. One such construct is comprises residues 19 to 397 of SEQ ID NO:2, fused to human Ig. znssp2 or znssp2-Ig chimeric proteins are used, for example, to identify the znssp2 anti-complementary molecule, including the natural anti-complementary molecule, as well as agonists and antagonists of the natural anti-complementary molecule. Using labeled soluble znssp2, cells expressing the anti-complementary molecule are identified by fluorescence immunocytometry or immunohistochemistry. The soluble fusion proteins or soluble Ig fusion protein is useful in studying the distribution of the anti-complementary molecule on tissues or specific cell lineages, and to provide insight into complementary molecule-anti-complementary molecule biology.

In an alternative approach, a soluble znssp2 extracellular anti-complementary molecule-binding region can be expressed as a chimera with immunoglobulin heavy chain constant regions, typically an $F_C$ fragment, which contains two constant region domains and a hinge region, but lacks the variable region. Such fusions are typically secreted as multimeric molecules, wherein the Fc portions are disulfide bonded to each other and two enzyme polypeptides are arrayed in close proximity to each other. Fusions of this type can be used to affinity purify the cognate substrate from solution, as an in vitro assay tool, to block signals in vitro by specifically titrating out anti-complementary molecule, and as antagonists in vivo by administering them to block anti-complementary molecule stimulation. To purify anti-complementary molecule, a znssp2-Ig fusion protein (chimera) is added to a sample containing the anti-complementary molecule under conditions that facilitate complementary moleucle-anti-complementary molecule binding (typically near-physiological temperature, pH, and ionic strength). The chimera-substrate complex is then separated by the mixture using protein A, which is immobilized on a solid support (e.g., insoluble resin beads). The anti-complementary molecule is then eluted using conventional chemical techniques, such as with a salt or pH gradient. In the alternative, the chimera itself can be bound to a solid support, with binding and elution carried out as above. For use in assays, the chimeras are bound to a support via the $F_C$ region and used in an ELISA format.

The present invention also includes "functional fragments" of znssp2 polypeptides and nucleic acid molecules encoding such functional fragments. Routine deletion analyses of nucleic acid molecules can be performed to obtain functional fragments of a nucleic acid molecule that encodes an znssp2 polypeptide. As an illustration, DNA molecules having the nucleotide sequences of SEQ ID NOs:1 and 12 can be digested with Bal31 nuclease to obtain a series of nested deletions. The fragments are then inserted into expression vectors in proper reading frame, and the expressed polypeptides are isolated and tested for cell-cell interactions, or for the ability to bind anti-znssp2 antibodies. One alternative to exonuclease digestion is to use oligonucleotide-directed mutagenesis to introduce deletions or stop codons to specify production of a desired fragment. Alternatively, particular fragments of an znssp2 gene can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2–5A synthetase induced by human interferon," in *Biological Interferon Systems, Proceedings of ISIR-TNO Meeting on Interferon Systems,* Cantell (ed.), pages 65–72 (Nijhoff 1987), Herschman, "The EGF Enzyme," in *Control of Animal Cell Proliferation,* Vol. 1, Boynton et al., (eds.) pages 169–199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of an znssp2 gene that has amino acid changes, compared with the amino acid sequences of SEQ ID NOs:2 and 13. A variant znssp2 gene can be identified on the basis of structure by determining the level of identity with nucleotide and amino acid sequences of SEQ ID NOs:1, 2, and 13, as discussed above. An alternative approach to identifying a variant gene on the basis of structure is to determine whether a nucleic acid molecule encoding a potential variant znssp2 gene can hybridize to a nucleic acid molecule having the nucleotide sequence of SEQ ID NO:1, as discussed above.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethyl-homocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in Xenopus oocytes by microinjection of mutated mRNA and chemically aminoacylated suppressor tRNAs (Turcatti et al., *J. Biol. Chem.* 271:19991–8, 1996). Within a third method, *E coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for znssp2 amino acid residues.

Essential amino acids in the polypeptides of the present invention can be identified according to procedures known in the art, such as site-directed mutagenesis or alanine-scanning mutagenesis (Cunningham and Wells, *Science* 244: 1081–5, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–708, 1996. Sites of galactosyltransferase activity and cell-cell interactions can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related galactosyltransferase molecules.

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed znssp2 DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., galactosyltransferase activity as evidenced by glycoprotein synthesis, or cell-cell interactions, such as intracellular signaling) can be recovered from the host cells and rapidly sequenced using modern equipment. These methods allow the rapid determination of the importance of individual amino acid residues in a polypeptide of interest, and can be applied to polypeptides of unknown structure.

Regardless of the particular nucleotide sequence of a variant znssp2 gene, the gene encodes a polypeptide that is characterized by its anti-complementary molecule binding activity, or by the ability to bind specifically to an anti-znssp2 antibody. More specifically, variant znssp2 genes encode polypeptides which exhibit greater than 75, 80, or 90%, of the activity of polypeptide encoded by the human znssp2 gene described herein.

Using the methods discussed herein, one of ordinary skill in the art can identify and/or prepare a variety of polypeptide fragments or variants of SEQ ID NO:2 or that retain the galactsyltransferase properties, or cell-cell interactions of the wild-type znssp2 protein. Such polypeptides may include additional amino acids from, for example, an extracellular ligand-binding domain of another member of the galactosyltransferase family as well as part or all of the transmembrane and intracellular domains. Additionally fragments of znssp2 may include additional amino acids from the catalytic site of the galactosyltransferase domains of other family members. Additional amino acids from affinity tags and the like may also be included.

For any znssp2 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise znssp2 variants based upon the nucleotide and amino acid sequences described herein. Accordingly, the present invention includes a computer-readable medium encoded with a data structure that provides at least one of the following sequences: SEQ ID NO:1, SEQ ID NO:2, SEQ ID NO:3, SEQ ID NO:12, SEQ ID NO:13, and SEQ ID NO:14. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

The znssp2 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a znssp2 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a znssp2 polypeptide into the secretory pathway of a host cell, a secretory signal sequence (also known as a leader sequence, prepro sequence or pre sequence) is provided in the expression vector. The secretory signal sequence may be that of znssp2, or may be derived from another secreted protein (e.g., t-PA) or synthesized de novo. The secretory signal sequence is operably linked to the znssp2 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

The native secretory signal sequence of the polypeptides of the present invention is used to direct other polypeptides into the secretory pathway. The present invention provides for such fusion polypeptides. A signal fusion polypeptide can be made wherein a secretory signal sequence derived from a znssp2 polypeptide is be operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–5, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980–90, 1989; Wang and Finer, *Nature Med.* 2:714–6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci.* (Bangalore) 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide,* London, Chapman & Hall; O'Reilly, D. R. et al., *Baculovirus Expression Vectors: A Laboratory Manual,* New York, Oxford University Press., 1994; and, Richardson, C. D., Ed., *Baculovirus Expression Protocols. Methods in Molecular Biology,* Totowa, N.J., Humana Press, 1995. A second method of making recombinant znssp2 baculovirus utilizes a transposon-based system described by Luckow (Luckow, V. A, et al., *J. Virol.* 67:4566–79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the znssp2 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case znssp2. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971–6, 1990; Bonning, B. C. et al., *J. Gen. Virol.* 75:1551–6, 1994; and, Chazenbalk, G. D., and Rapoport, B., *J. Biol. Chem.* 270:1543–9, 1995. In such transfer vector constructs, a short or long version of the basic protein promoter can be used. Moreover, transfer vectors can be constructed which replace the native znssp2 secretory signal sequences with secretory signal sequencesz derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native znssp2 secretory signal sequence. In addition, transfer vectors can include an in-frame fusion with DNA encoding an epitope tag at the C- or N-terminus of the expressed znssp2 polypeptide, for example, a Glu-Glu epitope tag (Grussenmeyer, T. et al., *Proc. Natl. Acad. Sci.* 82:7952–4, 1985). Using a technique known in the art, a transfer vector containing znssp2 is transformed into *E. Coli,* and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses znssp2 is subsequently produced. Recombinant viral stocks are made by methods commonly used the art. The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., ibid.; Richardson, C. D., ibid.). Subsequent purification of the znssp2 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Patent No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a znssp2 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant znssp2 polypeptides (or chimeric znssp2 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor and receptor-like complementary polypeptides to support media are well known in the art. Selection of a particular method is a matter of routine design and is determined in part by the properties of the chosen support. See, for example, *Affinity Chromatography: Principles & Methods,* Pharmacia LKB Biotechnology, Uppsala, Sweden, 1988.

The polypeptides of the present invention can be isolated by a combination of procedures including, but not limited to, anion and cation exchange chromatography, size exclusion, and affinity chromatography. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.,* Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., maltose-binding protein, an immunoglobulin domain) may be constructed to facilitate purification.

To direct the export of a receptor polypeptide from the host cell, the receptor DNA is linked to a second DNA segment encoding a secretory peptide, such as a t-PA secretory peptide or a znssp2 secretory peptide. To facilitate purification of the secreted receptor polypeptide, a C-terminal extension, such as a poly-histidine tag, substance P, Flag peptide (Hopp et al., *Bio/Technology* 6:1204–1210, 1988; available from Eastman Kodak Co., New Haven, Conn.) or another polypeptide or protein for which an antibody or other specific binding agent is available, can be fused to the receptor polypeptide.

Moreover, using methods described in the art, polypeptide fusions, or hybrid znssp2 proteins, are constructed using regions or domains of the inventive znssp2 in combination with those of other human galactosyltransferase family proteins (e.g. HSGALT3, HSGALT4, β3Gal-T2, and β3Gal-T3, or the human species ortholog of Brainiac), or heterologous proteins (Sambrook et al., ibid., Altschul et al., ibid., Picard, *Cur. Opin. Biology,* 5:511–5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between znssp2 of the present invention with the functionally equivalent domain(s) from another family member, such as the human species ortholog of Brainiac, or other galactosyltransferases, etc. Such domains include, but are not limited to, the hydrophobic region thought to be a putative secretory signal sequence or transmembrane domain (residues 1 to 18 of SEQ ID NO:2), and other conserved motifs such as the β1→3 GalTase homology region (residues 148 to 397 of SEQ ID NO:2), and significant domains or regions in this family. Such fusion proteins would be expected to have a biological functional profile that is the same or similar to polypeptides of the present invention or other known galactosyltransferase family proteins (e.g. HSGALT3, HSGALT4, and Brainiac), depending on the fusion constructed. Moreover, such fusion proteins may exhibit other properties as disclosed herein.

Znssp2 polypeptides or fragments thereof may also be prepared through chemical synthesis. Znssp2 polypeptides may be monomers or multimers; glycosylated or non-glycosylated; pegylated or non-pegylated; and may or may not include an initial methionine amino acid residue.

Znssp2 polypeptides of the present invention can also be synthesized by exclusive solid phase synthesis, partial solid phase methods, fragment condensation or classical solution synthesis. The polypeptides are preferably prepared by solid phase peptide synthesis, for example as described by Merrifield, *J. Am. Chem. Soc.* 85:2149, 1963. The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aryl type protecting groups (e.g., biotinyl), aromatic urethane type protecting groups [e.g., benzyloxycarbonyl (Cbz), substituted benzyloxycarbonyl and 9-fluorenylmethyloxy-carbonyl (Fmoc)], aliphatic urethane protecting groups [e.g., t-butyloxycarbonyl (tBoc), isopropyloxycarbonyl, cyclohexloxycarbonyl] and alkyl type protecting groups (e.g., benzyl, triphenylmethyl). The preferred protecting groups are tBoc and Fmoc,. thus the peptides are said to be synthesized by tBoc and Fmoc chemistry, respectively.

The side-chain protecting groups selected must remain intact during coupling and not be removed during the deprotection of the amino-terminus protecting group or during coupling conditions. The side-chain protecting groups must also be removable upon the completion of synthesis using reaction conditions that will not alter the finished polypeptide. In tBoc chemistry, the side-chain protecting groups for trifunctional amino acids are mostly benzyl based. In Fmoc chemistry, they are mostly tert-butyl or trityl based.

In tBoc chemistry, the preferred side-chain protecting groups are tosyl for arginine, cyclohexyl for aspartic acid, 4-methylbenzyl (and acetamidomethyl) for cysteine, benzyl for glutamic acid, serine and threonine, benzyloxymethyl (and dinitrophenyl) for histidine, 2-Cl-benzyloxycarbonyl for lysine, formyl for tryptophan and 2-bromobenzyl for tyrosine. In Fmoc chemistry, the preferred side-chain protecting groups are 2,2,5,7,8-pentamethylchroman-6-sulfonyl (Pmc) or 2,2,4,6,7-pentamethyldihydrobenzofuran-5-sulfonyl (Pbf) for arginine, trityl for asparagine, cysteine, glutamine and histidine, tert-butyl for aspartic acid, glutamic acid, serine, threonine and tyrosine, tBoc for lysine and tryptophan.

For the synthesis of phosphopeptides, either direct or post-assembly incorporation of the phosphate group is used. In the direct incorporation strategy, the phosphate group on serine, threonine or tyrosine may be protected by methyl, benzyl, or tert-butyl in Fmoc chemistry or by methyl, benzyl or phenyl in tBoc chemistry. Direct incorporation of phosphotyrosine without phosphate protection can also be used in Fmoc chemistry. In the post-assembly incorporation strategy, the unprotected hydroxyl groups of serine, threonine or tyrosine are derivatized on solid phase with di-tert-butyl-, dibenzyl- or dimethyl-N,N'-diisopropylphosphoramidite and then oxidized by tert-butylhydroperoxide.

Solid phase synthesis is usually carried out from the carboxyl-terminus by coupling the alpha-amino protected (side-chain protected) amino acid to a suitable solid support. An ester linkage is formed when the attachment is made to a chloromethyl, chlortrityl or hydroxymethyl resin, and the resulting polypeptide will have a free carboxyl group at the C-terminus. Alternatively, when an amide resin such as benzhydrylamine or p-methylbenzhydrylamine resin (for tBoc chemistry) and Rink amide or PAL resin (for Fmoc chemistry) are used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available, and their preparations have been described by Stewart et al., "Solid Phase Peptide Synthesis" (2nd Edition), (Pierce Chemical Co., Rockford, Ill., 1984) and Bayer & Rapp Chem. Pept. Prot. 3:3 (1986); and Atherton et al., Solid Phase Peptide Synthesis: *A Practical Approach*, IRL Press, Oxford, 1989.

The C-terminal amino acid, protected at the side chain if necessary, and at the alpha-amino group, is attached to a hydroxylmethyl resin using various activating agents including dicyclohexylcarbodiimide (DCC), N,N'-diisopropylcarbodiimide (DIPCDI) and carbonyldiimidazole (CDI). It can be attached to chloromethyl or chlorotrityl resin directly in its cesium tetramethylammonium salt form or in the presence of triethylamine (TEA) or diisopropylethylamine (DIEA). First amino acid attachment to an amide resin is the same as amide bond formation during coupling reactions.

Following the attachment to the resin support, the alpha-amino protecting group is removed using various reagents depending on the protecting chemistry (e.g., tBoc, Fmoc). The extent of Fmoc removal can be monitored at 300–320 nm or by a conductivity cell. After removal of the alpha-amino protecting group, the remaining protected amino acids are coupled stepwise in the required order to obtain the desired sequence.

Various activating agents can be used for the coupling reactions including DCC, DIPCDI, 2-chloro-1,3-dimethylimidium hexafluorophosphate (CIP), benzotriazol-1-yl-oxy-tris-(dimethylamino)-phosphonium hexafluorophosphate (BOP) and its pyrrolidine analog (PyBOP), bromo-tris-pyrrolidino-phosphonium hexafluorophosphate (PyBroP), O-(benzotriazol-1-yl)-1,1,3,3-tetramethyl-uronium hexafluorophosphate (HBTU) and its tetrafluoroborate analog (TBTU) or its pyrrolidine analog (HBPyU), O-(7-azabenzotriazol-1-yl)-1,1,3,3-tetramethyl-uronium hexafluorophosphate (HATU) and its tetrafluoroborate analog (TATU) or its pyrrolidine analog (HAPyU). The most common catalytic additives used in coupling reactions include 4-dimethylaminopyridine (DMAP), 3-hydroxy-3,4-dihydro-4-oxo-1,2,3-benzotriazine (HODhbt), N-hydroxybenzotriazole (HOBt) and 1-hydroxy-7-azabenzotriazole (HOAt). Each protected amino acid is used in excess (>2.0 equivalents), and the couplings are usually carried out in N-methylpyrrolidone (NMP) or in DMF, CH2Cl2 or mixtures thereof. The extent of completion of the coupling reaction can be monitored at each stage, e.g., by the ninhydrin reaction as described by Kaiser et al., *Anal. Biochem.* 34:595, 1970. In cases where incomplete coupling is found, the coupling reaction is extended and repeated and may have chaotropic salts added. The coupling reactions can be performed automatically with commercially available instruments such as ABI model 430A, 431A and 433A peptide synthesizers.

After the entire assembly of the desired peptide, the peptide-resin is cleaved with a reagent with proper scavengers. The Fmoc peptides are usually cleaved and deprotected by TFA with scavengers (e.g., H2O, ethanedithiol, phenol and thioanisole). The tBoc peptides are usually cleaved and deprotected with liquid HF for 1–2 hours at −5 to 0° C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of tryptophan and the dinitrophenyl group of histidine need to be removed, respectively by piperidine and thiophenyl in DMF prior to the HF cleavage. The acetamidomethyl group of cysteine can be removed by mercury(II)acetate and alternatively by iodine, thallium(III)trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyltrifluoroacetate (TMSOTf).

The activity of molecules of the present invention can be measured using a variety of assays that measure, for example, cell-cell interactions, glycolipid and glycoprotein biosynthesis, development, and other biological functions associated with galactosyltransferase family members. Of particular interest are changes in the transfer of galactosyl molecules in glycoprotein synthesis and in cell-cell interactions in pancreas, colon, or small intestine tissue cell lines derived from these tissues. Such assays are well known in the art. For a general reference, see Kolbinger, F. et al., *J. Biol. Chem.* 273: 433–440, 1998; Amado, M. et al., *J. Biol. Chem.* 273:12770–12778, 1998; Hennet, T. et al., *J. Biol. Chem.* 273:58–65, 1998; and Ram B. P., and Munjal, D. D., *CRC Crit. Rev. Biochem.* 17:257–311, 1985. Of additional interest are differences in cellular expression of znssp2 in diseased versus non-diseased tissues. Specific assays include, but are not limited to bioassays measuring cell migration, contact inhibition, tissue interactions, and metastasis. Additional assays would measure neuronal specificity, fertilization, embryonic cell adhesions, limb bud morphogenesis, mesenchyme development, immune recognition, growth control, tumor metastasis and suppression, and intracellular and extracellular glycoprotein and glycolipid biosynthesis.

Additional activities likely associated with the polypeptides of the present invention include proliferation of cells of the pancreas, colon, spinal cord, bone marrow, small intestine, peripheral leukocytes, bladder, prostate, myometrium, and breast directly or indirectly through other growth factors; action as a chemotaxic factor; and as a factor for expanding pancreas and mesenchymal stem cell and precursor populations.

Another assay of interest measures or detects changes in proliferation, differentiation, and development. Proliferation can be measured using cultured primary pancreas cells, ex plant tissues, or in vivo by administering molecules of the claimed invention to the appropriate cells, tissues, or animal models. Generally, proliferative effects are observed as an increase in cell number and therefore, may include inhibition of apoptosis, as well as mitogenesis. Likewise, a decrease in cell number and cell migration could be analyzed. Established cell lines can be established by one skilled in the art and are available from American Type Culture Collection (Manasas, Va.). Assays measuring cell proliferation are well known in the art. For example, assays measuring proliferation include such assays as chemosensitivity to neutral red dye (Cavanaugh et al., *Investigational New Drugs* 8:347–354, 1990,), incorporation of radiolabelled nucleotides (Cook et al., *Analytical Biochem.* 179:1–7, 1989,), incorporation of 5-bromo-2'-deoxyuridine (BrdU) in the DNA of proliferating cells (Porstmann et al., *J. Immunol. Methods* 82:169–179, 1985), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988).

Proliferation of bone marrow and peripheral blood lymphocyte cells can be assayed by harvesting these cells from mice, suspending the mononuclear cells in a base medium, and measuring proliferation in the presence of znssp2 protein. Similarly, clonogenic assays can be performed.

To determine if znssp2 is a chemotractant in vivo, znssp2 can be given by intradermal or intraperitoneal injection. Characterization of the accumulated leukocytes at the site of injection can be determined using lineage specific cell surface markers and fluorescence immunocytometry or by immunohistochemistry (Jose, *J. Exp. Med.* 179:881–87, 1994). Release of specific leukocyte cell populations from bone marrow into peripheral blood can also be measured after znssp2 injection.

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors and receptor-like complementary molecules. The stage of a cell population's differentiation is monitored by identification of markers present in the cell population. Myocytes, osteoblasts, adipocytes, chrondrocytes, fibroblasts and reticular cells are believed to originate from a common mesenchymal stem cell (Owen et al., *Ciba Fdn. Symp.* 136:42–46, 1988). Markers for mesenchymal stem cells have not been well identified (Owen et al., *J. of Cell Sci.* 87:731–738, 1987), so identification is usually made at the progenitor and mature cell stages. The novel polypeptides of the present invention are useful for studies to isolate mesenchymal stem cells and pancreas progenitor cells, both in vivo and ex vivo.

There is evidence to suggest that factors that stimulate specific cell types down a pathway towards terminal differentiation or dedifferentiation affect the entire cell population originating from a common precursor or stem cell. Thus, znssp2 polypeptides may stimulate inhibition or proliferation of endocrine and exocrine cells of the pancreas, as well as, cells associated with the colon, spinal cord, bone marrow, heart, small intestine, and peripheral leukocytes. Molecules of the present invention may, while stimulating proliferation or differentiation of pancreas cells, inhibit proliferation or differentiation of other tissues, by virtue of their effect on common precursor/stem cells.

Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, 1989).

The znssp2 polypeptides of the present invention can be used to study pancreatic cell proliferation or differentiation. Such methods of the present invention generally comprise incubating α cells, β cells, δ cells, F cells and acinar cells in the presence and absence of znssp2 polypeptide, monoclonal antibody, agonist or antagonist thereof and observing changes in cell proliferation or differentiation. An exemplary model system to study the formation of pancreatic endocrine cells in vitro uses AR42J cells which are derived from acinar cells. Mashima, H. et al., *Endocrinology* 137:3969–3976, 1996.

Proteins, including alternatively spliced peptides, and fragments, of the present invention are useful for modulating cell-cell interactions, neuronal specificity, fertilization, morphogenesis, development, inflammation, tumorigenesis, immune recognition, growth control, tumor suppression, and glycoprotein and glycolipid biosynthesis. Znssp2 molecules, variants, and fragments can be applied in isolation, or in conjunction with other molecules (growth factors, cytokines, etc.) in pancreas, colon, spinal cord, bone marrow, heart, small intestine, and peripheral leukocytes. Alternative splicing of znssp2 may be cell-type specific and confer activity to specific tissues.

As exemplary cell line of the pancreas to test the activity of znssp2 is CRL-1682, an human pancreas adenocarcinoma cell line, (ATCC, Manassas, Va.).

Other assays to measure the effects of znssp2 include proliferation assays (i.e., of pancreas, bone marrow, spinal cord, colon, or small intestine) by testing tissue and cells from healthy volunteers with znssp2 protein, or a znssp2-free negative control for the ability of the tissue and cells to proliferate.

Proteins of the present invention are useful for delivery of therapeutic agents such as, but not limited to, radionuclides, chemotherapy agents, and small molecules. The effects of znssp2 can be measured in vitro using cultured cells, ex vivo on tissue slices, or in vivo by administering molecules of the claimed invention to the appropriate animal model. For instance, znssp2 transfected (or co-transfected) expression host cells may be embedded in an alginate environment and injected (implanted) into recipient animals. Alginate-poly-L-lysine microencapsulation, permselective membrane encapsulation and diffusion chambers have been described as a means to entrap transfected mammalian cells or primary mammalian cells. These types of non-immunogenic "encapsulations" or microenvironments permit the transfer of nutrients into the microenvironment, and also permit the diffusion of proteins and other macromolecules secreted or released by the captured cells across the environmental barrier to the recipient animal. Most importantly, the capsules or microenvironments mask and shield the foreign, embedded cells from the recipient animal's immune response. Such microenvironments can extend the life of the injected cells from a few hours or days (naked cells) to several weeks (embedded cells).

Alginate threads provide a simple and quick means for generating embedded cells. The materials needed to generate the alginate threads are readily available and relatively inexpensive. Once made, the alginate threads are relatively strong and durable, both in vitro and, based on data obtained using the threads, in vivo. The alginate threads are easily manipulable and the methodology is scalable for preparation of numerous threads. In an exemplary procedure, 3% alginate is prepared in sterile $H_2O$, and sterile filtered. Just prior to preparation of alginate threads, the alginate solution is again filtered. An approximately 50% cell suspension (containing about $5 \times 10^5$ to about $5 \times 10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle attached). A large bore needle is then attached to the syringe, and the thread is intraperitoneally injected into a recipient in a minimal volume of the Lactated Ringer's Solution.

An alternative in vivo approach for assaying proteins of the present invention involves viral delivery systems. Exemplary viruses for this purpose include adenovirus, herpesvirus, lentivirus, vaccinia virus and adeno-associated virus (AAV). Adenovirus, a double-stranded DNA virus, is currently the best studied gene transfer vector for delivery of heterologous nucleic acid (for a review, see T. C. Becker et al., *Meth. Cell Biol.* 43:161–89, 1994; and J. T. Douglas and D. T. Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see Garnier et al., *Cytotechnol.* 15:145–55, 1994). With either protocol, an expressed, secreted heterologous protein can be repeatedly isolated from the cell culture supernatant. Within the infected 293S cell production protocol, non-secreted proteins may also be effectively obtained.

In view of the tissue distribution (i.e., pancreas, colon, spinal cord, bone marrow, small intestine, peripheral leukocytes, and various other tissues) observed for znssp2, agonists (including the natural ligand/substrate/cofactor/etc.) and antagonists have enormous potential in both in vitro and in vivo applications. Compounds identified as znssp2 agonists are useful for studying galactosylation of cell surface antigens as well as cell-cell interactions in vitro and in vivo. For example, znssp2 and agonist compounds are useful as components of defined cell culture media, and may be used alone or in combination with other cytokines and hormones to replace serum that is commonly used in cell culture. Agonists are thus useful in specifically promoting the growth and/or development of pancreas, colon, spinal cord, bone marrow, small intestine, and peripheral leukocytes in culture. Alternatively, znssp2 polypeptides and znssp2 agonist polypeptides are useful as a research reagent, particularly for the growth and expansion of pancreas, colon or small intestine cells. Znssp2 polypeptides are added to tissue culture media for these cell types.

Additionally, molecules of the present invention can be used in vitro to modify glycoproteins. Aberrant glycosylation can be modified by the application of the proteins of the present invention. Znssp2 molecules can be added in vitro to production or reagent grade proteins to modify the improper galactosylation of proteins. Additionally, molecules of the present invention can be used in the production of properly glycosylated saccharide chains.

Antagonists are also useful as research reagents for characterizing sites of interactions between member of complement/anti-complement pairs as well as site of galactosyltransferase catalysis.

Inhibitors of znssp2 activity (znssp2 antagonists) include anti-znssp2 antibodies and soluble znssp2 molecules, as well as other peptidic and non-peptidic agents (including ribozymes).

The invention also provides antagonists, which either bind to znssp2 polypeptides or, alternatively, to a anti-complementary molecule to which znssp2 polypeptides bind, thereby inhibiting or eliminating the function of znssp2. Such znssp2 antagonists would include antibodies; polypeptides which bind either to the znssp2 polypeptide or to its anti-complementary molecule or natural or synthetic analogs of znssp2 anti-complementary molecule which retain the ability to bind the anti-complementary molecule but do not result in glycoprotein or glycolipid synthesis or cell-cell interactions. Such analogs could be peptides or peptide-like compounds. Natural or synthetic small molecules which bind to znssp2 polypeptides and prevent glyprotein or glycolipid synthesis or cell-cell interactions are also contemplated as antagonists. Also contemplated are soluble znssp2 polypeptides. As such, znssp2 antagonists would be useful as therapeutics for treating certain disorders where blocking glycosylation or binding of the znssp2-anti-complementary molecule would be beneficial.

Znssp2 polypeptides may be used within diagnostic systems to detect the presence of znssp2 anti-complementary molecule polypeptides. Antibodies or other agents that specifically bind to znssp2 or its anti-complementary molecule may also be used to detect the presence of circulating znssp2 or anti-complementary molecule polypeptides. Such detection methods are well known in the art and include, for example, enzyme-linked immunosorbent assay (ELISA) and radioimmunoassay. Immunohistochemically labeled znssp2 antibodies can be used to detect znssp2 and/or znssp2 anti-complementary molecule in tissue samples. znssp2 levels can also be monitored by such methods as RT-PCR, where znssp2 mRNA can be detected and quantified. The information derived from such detection methods would provide insight into the significance of znssp2 polypeptides in various diseases, and as such would serve as diagnostic tools for diseases for which altered levels of znssp2 are significant. Altered levels of znssp2 polypeptides may be indicative of pathological conditions including, for example, cancer, auto-immune diseases, digestive disordersm and inflammatory disorders.

A "soluble protein" is a protein that is not bound to a cell membrane. Soluble proteins are most commonly anti-complementary molecule-binding polypeptides that lack transmembrane and cytoplasmic domains. Soluble proteins can comprise additional amino acid residues, such as affinity tags that provide for purification of the polypeptide or provide sites for attachment of the polypeptide to a substrate, or immunoglobulin constant region sequences. Many cell-surface proteins have naturally occurring, soluble counterparts that are produced by proteolysis or translated from alternatively spliced mRNAs. Proteins are said to be substantially free of transmembrane and intracellular polypeptide segments when they lack sufficient portions of these segments to provide membrane anchoring or signal transduction, respectively.

Soluble forms of znssp2 polypeptides may act as antagonists to or agonists of znssp2 polypeptides, and would be useful to modulate the effects of znssp2 in pancreas, colon and small intestine. The soluble form of znssp2 does not contain a transmembrane domain (i.e., the polypeptide of residues 19 to 397 of SEQ ID NO:2) and may act as an agonist or antagonist of znssp2 activity. Since polypeptides of this nature are not anchored to the membrane, they can act at sites distant from the tissues in which they are expressed. Thus, the activity of the soluble form of znssp2 polypeptides can be more wide spread than its membrane-anchored counterpart. Both isoforms would be useful in studying the effects of the present invention in vitro an in vivo.

Znssp2 can also be used to identify inhibitors (antagonists) of its activity. Test compounds are added to the assays disclosed herein to identify compounds that inhibit the activity of znssp2. In addition to those assays disclosed herein, samples can be tested for inhibition of znssp2 activity within a variety of assays designed to measure complementary molecule-anti-complementary molecule binding or the stimulation/inhibition of znssp2-dependent cellular responses. For example, znssp2-responsive cell lines can be transfected with a reporter gene construct that is responsive to a znssp2-stimulated cellular pathway. Reporter gene constructs of this type are known in the art, and will generally comprise a znssp2-DNA response element operably linked to a gene encoding an assayable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6; 1988 and Habener, *Molec. Endocrinol.* 4 (8):1087–94; 1990. Hormone response elements are reviewed in Beato, *Cell* 56:335–44; 1989. Candidate compounds, solutions, mixtures or extracts are tested for the ability to inhibit the activity of znssp2 on the target cells as evidenced by a decrease in znssp2 stimulation of reporter gene expression. Assays of this type will detect compounds that directly block znssp2 binding to anti-complementary molecules, as well as compounds that block processes in the cellular pathway subsequent to this binding. In the alternative, compounds or other samples can be tested for direct blocking of znssp2 binding to its anti-complementary molecule using znssp2 tagged with a detectable label (e.g., $^{125}$I, biotin, horseradish peroxidase, FITC, and the like). Within assays of this type, the ability of a test sample to inhibit the binding of labeled znssp2 to the anti-complementary molecule is indicative of inhibitory activity, which can be confirmed through secondary assays. Complementary molecules used within binding assays may be cellular complementary molcuels or isolated, immobilized complementary molecules, or receptor-like complementary molecules.

Assays measuring the inhibition of galactosyltransferase activity in glycoprotein synthesis are listed in Ram, B. P., (ibid).

Also, znssp2 polypeptides, agonists or antagonists thereof may be therapeutically useful for promoting wound healing, for example, in the pancreas. To verify the presence of this capability in znssp2 polypeptides, agonists or antagonists of the present invention, such znssp2 polypeptides, agonists or antagonists are evaluated with respect to their ability to facilitate wound healing according to procedures known in the art. If desired, znssp2 polypeptide performance in this regard can be compared to growth factors, such as EGF, NGF, TGF-α, TGF-β, insulin, IGF-I, IGF-II, fibroblast growth factor (FGF) and the like. In addition, znssp2 polypeptides or agonists or antagonists thereof may be evaluated in combination with one or more growth factors to identify synergistic effects.

A znssp2 polypeptide can be expressed as a fusion with an immunoglobulin heavy chain constant region, typically an $F_C$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in closed proximity to each other. Fusions of this type can be used to evaluate specific donor/acceptor molecules, affinity purify ligands, or use as an in vitro assay tool. This fusion can also be used to determine the homodimerization potential for znssp2. For use in assays, the chimeras are bound to a support via the $F_C$ region and used in an ELISA format.

A znssp2 ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column or chip, and fluids containing ligand are passed through the column or chip one or more times to allow ligand to bind to the receptor or receptor-like complementary polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Znssp2 polypeptides can also be used within other assay systems known in the art. Such systems include Scatchard analysis for determination of binding affinity (see Scatchard, *Ann. N.Y. Acad. Sci.* 51: 660–72, 1949) and calorimetric assays (Cunningham et al., *Science* 253:545–48, 1991; Cunningham et al., Science 245:821–25, 1991).

Within the polypeptides of the present invention are polypeptides that comprise an epitope-bearing portion of a protein as shown in SEQ ID NOs:2 and 13.

An "epitope" is a region of a protein to which an antibody can bind. See, for example, Geysen et al., *Proc. Natl. Acad. Sci. USA* 81:3998–4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., *Science* 219:660–666, 1983. Antibodies that recognize short, linear epitopes are particularly useful in analytic and diagnostic applications that employ denatured protein, such as Western blotting (Tobin, *Proc. Natl. Acad. Sci. USA* 76:4350–4356, 1979), or in the analysis of fixed cells or tissue samples. Antibodies to linear epitopes are also useful for detecting fragments of znssp2, such as might occur in body fluids or cell culture media.

Antigenic, epitope-bearing polypeptides of the present invention are useful for raising antibodies, including monoclonal antibodies, that specifically bind to a znssp2 protein. The znssp2 polypeptide or a fragment thereof serves as an antigen (immunogen) to inoculate an animal and elicit an immune response. One of skill in the art would recognize that antigenic, epitope-bearing polypeptides contain a sequence of at least six, or at least nine, or from 15 to about 30 contiguous amino acid residues of a znssp2 protein (e.g., SEQ ID NO:2). Polypeptides comprising a larger portion of a znssp2 protein, i.e. from 30 to 100 residues up to the entire sequence, are included. Antigens or immunogenic epitopes can also include attached tags, adjuvants and carriers, as described herein. Suitable antigens include the znssp2 polypeptides encoded by SEQ ID NO:2 from amino acid number 1 to amino acid number 397, or a contiguous 9 to 397 amino acid fragment thereof. Such regions include secretory sequence, the catalytic domain, or the transmembrane domain of znssp2 and fragments thereof. Polypeptides in this regard include those comprising residues 1 to 18 of SEQ ID NO:2; residues 19 to 147 of SEQ ID NO:2; residues 148 to 397 of SEQ ID NO:2; and residues 19 to 397 of SEQ ID NO:2.

The present invention also provides polypeptide fragments or peptides comprising an epitope-bearing portion of an znssp2 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides contain at least four to ten amino acids, or at least ten to fifteen amino acids, or 15 to 30 amino acids of SEQ ID NOs:2 or 13. Such epitope-bearing peptides and polypeptides can be produced by fragmenting an znssp2 polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology,* Vol. 10, Manson (ed.), pages 105–116 (The Humana Press, Inc. 1992), Price, "Production and Characterization of Synthetic Peptide-Derived Antibodies," in *Monoclonal Antibodies. Production, Engineering, and Clinical Application,* Ritter and Ladyman (eds.), pages 60–84 (Cambridge University Press 1995), and Coligan et al. (eds.), *Current Protocols in Immunology,* pages 9.3.1–9.3.5 and pages 9.4.1–9.4.11 (John Wiley & Sons 1997).

As an illustration, potential antigenic sites in human (SEQ ID NO:2) and mouse (SEQ ID NO:13) znssp2 were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

Suitable antigens of the human sequence include residue 1 to residue 6 of SEQ ID NO:2; residue 26 to residue 54 of SEQ ID NO:2; residue 82 to residue 94 of SEQ ID NO:2; residue 110 to residue 117 of SEQ ID NO:2; residue 122 to residue 127 of SEQ ID NO:2; residue 131 to residue 136 of SEQ ID NO:2; residue 139 to residue 146 of SEQ ID NO:2; residue 154 to residue 177 of SEQ ID NO:2; residue 187 to residue 197 of SEQ ID NO:2 ; residue 202 to residue 207 of SEQ ID NO:2; residue 282 to residue 289 of SEQ ID NO:2; residue 295 to residue 301 of SEQ ID NO:2; residue 358 to residue 365 of SEQ ID NO:2; and residue 387 to residue 397 of SEQ ID NO:2; or a portion thereof which contains a 4 to 10 amino acid segment. Hydrophilic peptides, such as those predicted by one of skill in the art from a hydrophobicity plot are also immonogenic. Znssp2 hydrophilic peptides include peptides comprising amino acid sequences selected from the group consisting of: residue 24 to residue 53 of SEQ ID NO:2; residue 72 to residue 81 of SEQ ID NO:2; residue 85 to residue 94 of SEQ ID NO:2; residue 109 to residue 115 of SEQ ID NO:2; residue 128 to residue 134 of SEQ ID NO:2; residue 156 to residue 173 of SEQ ID NO:2; residue 200 to residue 209 of SEQ ID NO:2; residue 281 to residue 291 of SEQ ID NO:2; residue 297 to residue 306 of SEQ ID NO:2; residue 359 to residue 367 of SEQ ID NO:2; and residue 387 to residue 397 of SEQ ID NO:2; or a portion thereof which contains a 4 to 10 amino acid segment. Additionally, antigens can be generated to portions of the polypeptide which are likely to be on the surface of the folded protein. These antigens include: residue 25 to residue 54 of SEQ ID NO:2; residue 57 to residue 62 of SEQ ID NO:2; residue 72 to residue 78 of SEQ ID NO:2; residue 84 to residue 93 of SEQ ID NO:2; residue 108 to residue 115 of SEQ ID NO:2; residue 155 to residue 167 SEQ ID NO:2; residue 202 to residue 207 of SEQ ID NO:2; residue 218 to residue 233 of SEQ ID NO:2; residue 281 to residue 287 of SEQ ID NO:2; residue 358 to residue 363 of SEQ ID NO:2; and residue 388 to residue 393 of SEQ ID NO:2; or a portion thereof which contains a 4 to 10 amino acid segment.

Suitable antigens based on the Jameson-Wolf method for the mouse sequence include residue 1 to residue 7 of SEQ ID NO:13; residue 26 to residue 52 of SEQ ID NO:13; residue 83 to residue 88 of SEQ ID NO:13; residue 125 to residue 132 of SEQ ID NO:13; residue 133 to residue 139 of SEQ ID NO:13; residue 146 to residue 152 of SEQ ID NO:13; residue 158 to residue 163 of SEQ ID NO:13; residue 183 to residue 189 of SEQ ID NO:13; residue 193 to residue 200 of SEQ ID NO:13; residue 209 to residue 215 of SEQ ID NO:13; residue 237 to residue 242 of SEQ ID NO:13; residue 273 to residue 281 of SEQ ID NO:13; residue 288 to residue 295 of SEQ ID NO:13; residue 351 to residue 360 of SEQ ID NO:13; and residue 369 to residue 374 of SEQ ID NO:13; or a portion thereof which contains a 4 to 10 amino acid segment. Hydrophilic peptides, such as those predicted by one of skill in the art from a hydrophobicity plot are also immonogenic. znssp2 hydrophilic peptides include peptides comprising amino acid sequences selected from the group consisting of: residue 1 to residue 6 of SEQ ID NO:13; residue 24to residue 53 of SEQ ID NO:13; residue 68 to residue 78 of SEQ ID NO:13; residue 148 to residue 15 4 of SEQ ID NO:13; residue 156 ti residue 164 of SEQ ID NO:13; residue 192 to residue 200 of SEQ ID NO:13; residue 208 to residue 215 of SEQ ID NO:13; residue 273 to residue 280 of SEQ ID NO:13; residue 288 to residue 298 of SEQ ID NO:13; and residue 351 to residue 359 of SEQ ID NO:13; or a portion thereof which contains a 4 to 10 amino acid segment. Additionally, antigens can be generated to portions of the polypeptide which are likely to be on the surface of the folded protein. These antigens include: residue 25 to residue 37 of SEQ ID NO:13; residue 42 to residue 52 of SEQ ID NO:13; residue 69 to residue 76 of SEQ ID NO:13; residue 157 to residue 163 of SEQ ID NO:13; residue 193 to residue 198 of SEQ ID NO:13; residue 210 to residue 215 SEQ ID NO:13; residue 271 to residue 278 of SEQ ID NO:13; and residue 350 to residue 356 of SEQ ID NO:13; or a portion thereof which contains a 4 to 10 amino acid segment.

Antibodies from an immune response generated by inoculation of an animal with the antigens listed above can be isolated and purified as described herein. Methods for preparing and isolating polyclonal and monoclonal antibodies are well known in the art. See, for example, *Current Protocols in Immunology,* Cooligan, et al. (eds.), National Institutes of Health, John Wiley and Sons, Inc., 1995; Sambrook et al., *Molecular Cloning: A Laboratory Manual, Second Edition,* Cold Spring Harbor, N.Y., 1989; and Hurrell, J. G. R., Ed., *Monoclonal Hybridoma Antibodies: Techniques and Applications,* CRC Press, Inc., Boca Raton, Fla., 1982. Antibodies generated from this immune response can be isolated and purified as described herein. Methods for preparing and isolating polyclonal and monoclonal antibodies are well known in the art. See, for example, *Current Protocols in Immunology,* Cooligan, et al. (eds.), National Institutes of Health, John Wiley and Sons, Inc., 1995; Sambrook et al., *Molecular Cloning: A Laboratory Manual, Second Edition,* Cold Spring Harbor, N.Y., 1989; and Hurrell, J. G. R., Ed., *Monoclonal Hybridoma Antibodies: Techniques and Applications,* CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a znssp2 polypeptide or a fragment thereof. The immunogenicity of a znssp2 polypeptide may be increased through the use of an adjuvant, such as alum (aluminum hydroxide) or Freund's adjuvant. Polypeptides useful for immunization also include fusion polypeptides, such as fusions of znssp2 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to znssp2 protein or peptide, and selection of antibody display libraries in phage or similar vectors (for instance, through use of immobilized or labeled znssp2 protein or peptide). Genes encoding polypeptides having potential znssp2 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the znssp2 sequences disclosed herein to identify proteins which bind to znssp2. These "binding proteins" which interact with znssp2 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as znssp2 "antagonists" to block znssp2 binding and signal transduction in vitro and in vivo. These anti-znssp2 binding proteins would be useful for mediating galactosyltransferase activity extracellularly, therefore, mediating cell-cell interactions, such as, for example, tumor formation and metastasis, proliferation and differentiation, as well as glycoprotein and glycolipid synthesis.

As used herein, the term "binding proteins" additionally includes antibodies to znssp2 polypeptides, the cognate anti-complementary molecule of znssp2 polypeptides, proteins useful for purification of znssp2 polypeptides, and proteins associated with the catalytic (residues 19 to 397 of SEQ ID NO:2).

Antibodies are determined to be specifically binding if: 1) they exhibit a threshold level of binding activity, and/or 2) they do not significantly cross-react with related polypeptide molecules. First, antibodies herein specifically bind if they bind to a znssp2 polypeptide, peptide or epitope with a binding affinity ($K_a$) of $10^6$ M$^{-1}$ or greater, preferably $10^7$ M$^{-1}$ or greater, more preferably $10^8$ M$^{-1}$ or greater, and most preferably $10^9$ M$^{-1}$ or greater. The binding affinity of an antibody can be readily determined by one of ordinary skill in the art, for example, by Scatchard analysis (Scatchard, G., *Ann. NY Acad. Sci.* 51: 660–672, 1949).

Second, antibodies are determined to specifically bind if they do not significantly cross-react with related polypeptides. Antibodies do not significantly cross-react with related polypeptide molecules, for example, if they detect znssp2 but not known related polypeptides using a standard Western blot analysis (Ausubel et al., ibid.). Examples of known related polypeptides are orthologs, proteins from the same species that are members of a protein family, znssp2 polypeptides, and non-human znssp2. Moreover, antibodies may be "screened against" known related polypeptides to isolate a population that specifically binds to the inventive polypeptides. For example, antibodies raised to znssp2 are adsorbed to related polypeptides adhered to insoluble matrix; antibodies specific to znssp2 will flow through the matrix under the proper buffer conditions. Such screening allows isolation of polyclonal and monoclonal antibodies non-crossreactive to closely related polypeptides (*Antibodies: A Laboratory Manual,* Harlow and Lane (eds.), Cold Spring Harbor Laboratory Press, 1988; *Current Protocols in Immunology,* Cooligan, et al. (eds.), National Institutes of Health, John Wiley and Sons, Inc., 1995). Screening and isolation of specific antibodies is well known in the art. See, *Fundamental Immunology,* Paul (eds.), Raven Press, 1993; Getzoff et al., *Adv. in Immunol.* 43: 1–98, 1988; *Monoclonal Antibodies: Principles and Practice,* Goding, J. W. (eds.), Academic Press Ltd., 1996; Benjamin et al., *Ann. Rev. Immunol.* 2: 67–101, 1984.

A variety of assays known to those skilled in the art can be utilized to detect antibodies which specifically bind to znssp2 proteins or peptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant znssp2 protein or polypeptide.

Antibodies to znssp2 may be used for tagging cells that express znssp2; for isolating znssp2 by affinity purification;

in analytical methods employing FACS; for screening expression libraries; for generating anti-idiotypic antibodies; and as neutralizing antibodies or as antagonists to block znssp2 in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to znssp2 or fragments thereof may be used in vitro to detect denatured znssp2 or fragments thereof in assays, for example, Western Blots or other assays known in the art.

The soluble znssp2 is useful in studying the distribution of its anti-complentary molecule in tissues or specific cell lineages, and to provide insight into complementary molecule-anti-complentary molecule biology. Using labeled znssp2, cells expressing the anti-complentary molecule are identified by fluorescence immunocytometry or immunocytochemistry. Application may also be made of 7 the specificity of UDP-glycosyltransferases for their substrates.

Antibodies can be made to soluble, znssp2 polypeptides which are His or FLAG™ tagged. Alternatively, such polypeptides form a fusion protein with Human Ig. In particular, antiserum containing polypeptide antibodies to His-tagged, or FLAG™-tagged soluble znssp2 can be used in analysis of tissue distribution of znssp2 by immunohistochemistry on human or primate tissue. These soluble znssp2 polypeptides can also be used to immunize mice in order to produce monoclonal antibodies to a soluble human znssp2 polypeptide. Monoclonal antibodies to a soluble human znssp2 polypeptide can also be used to mimic anti-complentary molecule coupling, resulting in activation or inactivation of the complementary molecule-anti-complentary molecule pair. For instance, it has been demonstrated that cross-linking anti-soluble CD40 monoclonal antibodies provides a stimulatory signal to B cells that have been sub-optimally activated with anti-IgM or LPS, and results in proliferation and immunoglobulin production. These same monoclonal antibodies act as antagonists when used in solution by blocking activation of the receptor. Monoclonal antibodies to znssp2 can be used to determine the distribution, regulation and biological interaction of the znssp2 and its anti-complentary molecule pair on specific cell lineages identified by tissue distribution studies.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor, enzyme, receptor-like complementary molecule or antigen, respectively, for instance). More specifically, znssp2 polypeptides or anti-znssp2 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer or diseased cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/ cytotoxic molecule conjugates.

In another embodiment, znssp2-cytokine fusion proteins or antibody-cytokine fusion proteins can be used for enhancing in vivo killing of target tissues (for example, pancreas, colon, spinal cord, bone marrow, small intestine and peripheral leukocyte cancers), if the znssp2 polypeptide or anti-znssp2 antibody targets, for example, the hyperproliferative pancreas, colon, spinal cord, bone marrow, small intestine and peripheral leukocyte cells (See, generally, Hornick et al., *Blood* 89:4437–47, 1997). They described fusion proteins enable targeting of a cytokine to a desired site of action, thereby providing an elevated local concentration of cytokine. Suitable znssp2 polypeptides or anti-znssp2 antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

In yet another embodiment, if the znssp2 polypeptide or anti-znssp2 antibody targets vascular cells or tissues, such polypeptide or antibody may be conjugated with a radionuclide, and particularly with a beta-emitting radionuclide, to reduce restenosis. Such therapeutic approach poses less danger to clinicians who administer the radioactive therapy. The bioactive polypeptide or antibody conjugates described herein can be delivered intravenously, intraarterially or intraductally, or may be introduced locally at the intended site of action.

The bioactive polypeptide or antibody conjugates described herein can be delivered intravenously, intraarterially or intraductally, or may be introduced locally at the intended site of action.

znssp2 polynucleotides and/or polypeptides may be useful for regulating the maturation of UDP-glycosyltransferase substrate-bearing cells, such as fibroblasts, lymphocytes and hematopoietic cells. znssp2 polypeptides will also find use in mediating metabolic or physiological processes in vivo. The effects of a compound on proliferation and differentiation can be measured in vitro using cultured cells. Bioassays and ELISAs are available to measure cellular response to znssp2, in particular are those which measure changes in cytokine production as a measure of cellular response (see for example, *Current Protocols in Immunology* ed. John E. Coligan et al., NIH, 1996). Assays to measure other cellular responses, including glycoprotein and glycolipid biosynthesis and metabolism, and cell-cell interactions are known in the art.

The activity of znssp2 or a peptide to which znssp2 binds, can be measured by a silicon-based biosensor microphysiometer which measures the extracellular acidification rate or proton excretion associated with such protein interactions and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and enzyme or enzyme activation, and the like, can be measured by this method. See, for example, McConnell, H. M. et al., *Science* 257:1906–1912, 1992; Pitchford, S. et al., *Meth. Enzymol.* 228:84–108, 1997; Arimilli, S. et al., *J. Immunol. Meth.* 212:49–59, 1998; Van Liefde, I. et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including znssp2 proteins, their agonists, and antagonists. The microphysiometer can be used to measure responses of a znssp2-responsive eukaryotic cell, compared to a control eukaryotic cell that does not respond to znssp2 polypeptide. znssp2-responsive eukaryotic cells comprise cells into which a polynucleotide for znssp2 has been transfected creating a cell that is responsive to znssp2; or cells containing endogenous znssp2 polynucleotides. Differences, measured by a change in the response of cells exposed to znssp2 anti-complentary molecule, relative to a control not exposed to znssp2 anti-complentary molecule, directly measure the znssp2-modulated cellular responses. Moreover, such znssp2-modulated responses can be assayed under a variety of stimuli. The present invention provides a method of identifying agonists and antagonists of znssp2 protein, comprising providing cells responsive to a znssp2 polypeptide, culturing a first portion of the cells in the absence of a test compound, culturing a second portion of the cells in the presence of a test compound, and detecting a measurable change in a cellular response of the second portion of the cells as compared to the first portion of the cells. Moreover, culturing a third portion of the cells in the presence of znssp2 substrate and the absence of a test compound provides a positive control for the znssp2-responsive cells, and a control to compare the agonist activity of a test compound with that of the znssp2 substrate. Antagonists of znssp2 can be identified by exposing the cells to znssp2 substrate in the presence and absence of the test compound, whereby a reduction in znssp2-modulated activity is indicative of antagonist activity in the test compound.

Moreover, znssp2 can be used to identify cells, tissues, or cell lines which respond to a znssp2-modulated pathway. The microphysiometer, described above, can be used to rapidly identify cells responsive to znssp2 of the present invention. Cells can be cultured in the presence or absence of znssp2 polypeptide. Those cells which elicit a measurable change in extracellular acidification in the presence of znssp2 are responsive to znssp2. Such cell lines, can be used to identify znssp2 anti-complentary molecule, antagonists and agonists of znssp2 polypeptide as described above.

Molecules of the present invention can be used to identify and isolate receptors, ligands, or members of complement/anti-complement pairs involved in cell-cell interactions, and glycoprotein and glycolipid synthesis. For example, proteins and peptides of the present invention can be immobilized on a column and membrane preparations run over the column (*Immobilized Affinity Ligand Techniques,* Hermanson et al., eds., Academic Press, San Diego, Calif., 1992, pp.195–202). Proteins and peptides can also be radiolabeled (*Methods in Enzymol.*, vol. 182, "Guide to Protein Purification", M. Deutscher, ed., Acad. Press, San Diego, 1990, 721–37) or photoaffinity labeled (Brunner et al., *Ann. Rev. Biochem.* 62:483–514, 1993 and Fedan et al., *Biochem. Pharmacol.* 33:1167–80, 1984) and specific cell-surface proteins can be identified.

As a reagent, the polynucleotide encoding the amino acid residues from residue 333 to 338 of SEQ ID NO: 2, and the degenerate polynucleotide of SEQ ID NO:3, can be used to identify new family members. This would be useful in finding new galactosyltransferase and putative neurogenic secreted signaling peptides from the same or other tissues.

The polypeptides, nucleic acid and/or antibodies of the present invention can be used in treatment of disorders associated with cell migration, contact inhibition, tissue interactions, neuronal specificity, fertilization, embryonic cell adhesions, limb bud morphogenesis, mesenchyme development, immune recognition, inflammation, tumorigenesis, growth control, tumor metastasis, and intracellular and extracellular glycoprotein and glycolipid biosynthesis. The molecules of the present invention can be used to modulate glycoprotein synthesis and/or cell-cell interactions or to treat or prevent development of pathological conditions in such diverse tissue as pancreas, colon, spinal cord, bone marrow, heart, lung, spleen, prostate, small intestine, peripheral blood leukocytes, stomach, thyroid, trachea, placenta, skeletal muscle, kidney, lymph node, bladder, prostate, myometrium, spleen, and breast. In particular, certain pancreatic enzymatic deficiencies and malignancies, and pancreatic-cell mediated deficiencies may be amenable to such diagnosis, treatment or prevention.

Polynucleotides encoding znssp2 polypeptides are useful within gene therapy applications where it is desired to increase or inhibit znssp2 activity. If a mammal has a mutated or absent znssp2 gene, the znssp2 gene can be introduced into the cells of the mammal. In one embodiment, a gene encoding a znssp2 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a znssp2 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat.

No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993.

Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity; such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically. Similarly, the znssp2 polynucleotide itself can be used to target specific tissues.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Various techniques, including antisense and ribozyme methodologies, can be used to inhibit znssp2 gene transcription and translation, such as to inhibit cell proliferation in vivo. Polynucleotides that are complementary to a segment of a znssp2-encoding polynucleotide (e.g., a polynucleotide as set froth in SEQ ID NOs:1 or 12) are designed to bind to znssp2-encoding mRNA and to inhibit translation of such mRNA. Such antisense polynucleotides are used to inhibit expression of znssp2 polypeptide-encoding genes in cell culture or in a subject.

The present invention also provides reagents which will find use in diagnostic applications. For example, the znssp2 gene, a probe comprising znssp2 DNA or RNA or a subsequence thereof can be used to determine if the znssp2 gene is present on chromosome 19q13.2 or if a mutation has occurred. Detectable chromosomal aberrations at the znssp2 gene locus include, but are not limited to, aneuploidy, gene copy number changes, insertions, deletions, restriction site changes and rearrangements. These aberrations can occur within the coding sequence, within introns, or within flanking sequences, including upstream promoter and regulatory regions, and may be manifested as physical alterations within a coding sequence or changes in gene expression level. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid; Marian, *Chest* 108:255–65, 1995).

In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NOs:1 or 3, the complement of SEQ ID NOs:1 or 3, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient's genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34–8, 1991).

In addition, such polynucleotide probes could be used to hybridize to counterpart sequences on individual chromosomes. Chromosomal identification and/or mapping of the znssp2 gene could provide useful information about gene function and disease association. Many mapping techniques are available to one skilled in the art, for example, mapping somatic cell hybrids, and fluorescence in situ hybridization (FISH). One method is radiation hybrid mapping. Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows one to design PCR primers suitable for use with chromosomal radiation hybrid mapping panels. Radiation hybrid mapping panels are commercially available which cover the entire human genome, such as the Stanford G3 RH Panel and the GeneBridge 4 RH Panel (Research Genetics, Inc., Huntsville, Ala.). These panels enable rapid, PCR-based chromosomal localizations and ordering of genes, sequence-tagged sites (STSs), and other nonpolymorphic and polymorphic markers within a region of interest. This includes establishing directly proportional physical distances between newly discovered genes of interest and previously mapped markers. The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

Sequence tagged sites (STSs) can also be used independently for chromosomal localization. An STS is a DNA sequence that is unique in the human genome and can be used as a reference point for a particular chromosome or region of a chromosome. An STS is defined by a pair of oligonucleotide primers that are used in a polymerase chain reaction to specifically detect this site in the presence of all other genomic sequences. Since STSs are based solely on DNA sequence they can be completely described within an electronic database, for example, Database of Sequence Tagged Sites (dbSTS), GenBank, (National Center for Biological Information, National Institutes of Health, Bethesda, Md., and can be searched with a gene sequence of interest for the mapping data contained within these short genomic landmark STS sequences.

Transgenic mice, engineered to express the znssp2 gene, and mice that exhibit a complete absence of znssp2 gene function, referred to as "knockout mice" (Snouwaert et al., *Science* 257:1083, 1992), may also be generated (Lowell et al., *Nature* 366:740–42, 1993). These mice may be employed to study the znssp2 gene and the protein encoded thereby in an in vivo system.

Znssp2 polypeptides, variants, and fragments thereof, may be useful as replacement therapy for disorders associated with glycoprotein synthesis, functions of the digestive system, and cell-cell interactions.

A less widely appreciated determinant of tissue morphogenesis is the process of cell rearrangement: Both cell motility and cell-cell adhesion are likely to play central roles in morphogenic cell rearrangements. Cells need to be able to rapidly break and probably simultaneously remake contacts with neighboring cells. See Gumbiner, B. M., *Cell* 69:385–387, 1992. As a secreted protein in tissues of the pancreas, colon, small intestine, etc., znssp2 can play a role in intercellular rearrangement in these and other tissues.

The znssp2 polypeptide is expressed in tissues of the pancreas, colon, spinal cord, bone marrow, small intestine, and peripheral leukocytes. Thus, the polypeptides of the present invention are useful in studying cell adhesion and the role thereof in metastasis and may be useful in preventing metastasis, in particular metastasis in tumors of the pancreas, colon, spinal cord, bone marrow, small intestine, and peripheral leukocytes. Similarly, polynucleotides and polypeptides of znssp2 may be used to replace their defective counterparts in tumor or diseased tissues. Thus, znssp2 polypeptide pharmaceutical compositions of the present invention may be useful in prevention or treatment of disorders associated with pathological regulation or the expansion of these tissues. The polynucleotides of the present invention may also be used in conjunction with a regulatable promoter, thus allowing the dosage of delivered protein to be regulated.

Moreover, the activity and effect of znssp2 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Tumor models include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly M S, et al. *Cell* 79: 315–328,1994). C57BL6/J mice are treated with an experimental agent either through daily injection of recombinant protein, agonist or antagonist or a one time injection of recombinant adenovirus. Three days following this treatment, $10^5$ to $10^6$ cells are implanted under the dorsal skin. Alternatively, the cells themselves may be infected with recombinant adenovirus, such as one expressing znssp2, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500–1800 $mm^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., znssp2, on the ability of the tumor to recruit vasculature and undergo metastasis can thus be assessed. In addition, aside from using adenovirus, the implanted cells can be transiently transfected with znssp2. Moreover, purified znssp2 or znssp2-conditioned media can be directly injected in to this mouse model, and hence be used in this system. Use of stable znssp2 transfectants as well as use of induceable promoters to activate znssp2 expression in vivo are known in the art and can be used in this system to assess znssp2 induction of metastasis. For general reference see, O'Reilly M S, et al. *Cell* 79:315–328, 1994; and Rusciano D, et al. Murine Models of Liver Metastasis. *Invasion Metastasis* 14:349–361, 1995.

Tn-syndrome, also called Permanent Mixed-Field Polyagglutinability, is a very rare acquired disorder affecting all hematopoietic lineages. This syndrome is characterized by the expression of the Tn and sialosyl-Tn antigens on the cell surface. The Tn antigen has been identified as an unsubstituted α-linked N-acetyl-galactosamine linked O-glycosidically to threonine or serine residues of membrane proteins. In healthy blood, this sugar is substituted by galactose and sialic acid to form a tetrasaccharide. This Tn antigen may be a result of a deficiency in $\beta,1\rightarrow3$, galactosyltransferase. Expression of the Tn antigen along with the sialosyl-Tn antigen and a TF antigen (characterized by a deficiency in $\alpha,2\rightarrow3$, sialyl-transferase) have been recognized as a cancer-associated phenomenon for many years. See Berger, E. G. et al., *Transfus. Clin. Biol.* 2:103–108, 1994.

Thus, the study of this syndrome has been useful in elucidating the biology of carbohydrate glycosylation disorders and the appearance of cryptantigens on the cell surface, and cancer. Highly specific and complex tumor glycan antigens are likely of great interest in studying tissue specific tumors and znssp2 can be useful for studying tumors of the pancreas, colon, spinal cord, bone marrow, small intestine, and peripheral leukocytes.

Itzkowitz, et al., looked at the expression of these cryptantigens in tissues from normal, chronic pancreatitic, and pancreatic cancer patients. The sialosyl-Tn antigen is expressed in 97% of malignant, but 0% of normal tissues. The authors suggest that normal pancreas tissue is preferentially galactosylated resulting in less silaosyl-Tn antigen.

In malignant tissue, conditions favor the sialylation of Tn antigens thereby accounting for enhanced expression of sialosyl Tn over T anitgens.

In view of the high expression of znssp2 in the pancreas, and colon in normal tissue, a defect in the znssp2 gene may result in defective galactosylation of cell surface carbohydrates of pancreatic cells, leading to over sialylation of the Tn antigen, or over galactosylation of cellular antigens, in general. Thus, znssp2 polypeptides would be useful as a pancreas- or colon-specific β,1→3, galactosyltransferase replacement therapy for pre-cancerous and cancer tissues. To verify the presence of such activity in znssp2 containing normal cell lines and tumor cell lines, such cell lines are evaluated with respect to the presence of the Tn antigen according to procedures known in the art. See, for example, Berger et al., ibid., Itzkowitz et al., ibid. and the like.

Additionally, the lack of conditions favoring proper galactosylation may result in an increase in sialosyl Tn antigens in tissues expressing znssp2, which may cause an autoimmune reaction resulting in an immune attack on the pancreas, colon, spinal cord, bone marrow, small intestine, and peripheral leukocytes. In these cases, znssp2 molecules may be used to encourage proper galactosylation and limit the antigenic recognition in tissues over expressing the sialosyl Tn antigen.

Similarly, a defective znssp2 gene may result in improper glycoslation of the surface carbohydrates of the tissues of pancreas, colon, spinal cord, bone marrow, small intestine, and peripheral leukocytes, thus affecting cell-cell interactions and possibly cell cycle regulation. Such cases could be treated by administering polypeptides of znssp2 to mammals with such a defective gene.

Exocrine cells of the pancreas are important for the production of necessary enzymes involved in digestion. Persons defective in the znssp2 gene may be unable to properly digest food and and nutrients. Polynucleotides of znssp2 may be useful in treating a defective pancreatic specific β,1→3, galactosyl-transferase gene by gene therapy. Likewise, polypeptides of the present invention could be administered to a mammal as replacement therapy for a defective digestive enzyme.

Znssp2 gene may be useful to as a probe to identify humans who have a defective pancreatic or colonic specific β,1→3, galactosyltransferase gene. The strong expression of znssp2 in pancreas, and colon suggests that znssp2 polynucleotides or polypeptides are down-regulated in tumor, malignant, or immune-responding tissues. Thus, polynucleotides and polypeptides of znssp2, and mutations to them, can be used a indicators of pancreatic and colonic cancer, and disease, in diagnosis.

As a protein showing strong expression in the pancreas and colon, additional applications are to modulate gastric secretion in the treatment of acute pancreatitis and gastrointestinal disorders.

The polypeptides, nucleic acid, and/or antibodies of the present invention may be used in treatment of disorders associated with pancreas, diabetes, hypoglycemia; digestive systems including pancreas, colon, and small intestine; neuronal tissues, bone marrow, and peripheral leukocytes; and in disorders associated with glycoprotein synthesis. The molecules of the present invention may used to modulate or to treat or prevent development of pathological conditions in such diverse tissue as pancreas, colon, spinal cord, heart and bone marrow. In particular, certain syndromes or diseases may be amenable to such diagnosis, treatment or prevention.

The znssp2 polypeptide is expressed in the pancreas. Thus, znssp2 polypeptide pharmaceutical compositions of the present invention may be useful in prevention or treatment of pancreatic disorders associated with pathological regulation of the expansion of neuroendocrine and exocrine cells in the pancreas, such as IDDM, pancreatic cancer, pathological regulation of blood glucose levels, insulin expression, insulin resistance or digestive function.

The znssp2 polypeptide of the present invention may act in the neuroendocrine/exocrine cell fate decision pathway and may therefore be capable of regulating the expansion of neuroendocrine and exocrine cells in the pancreas. One such regulatory use is that of islet cell regeneration. Also, it has been hypothesized that the autoimmunity that triggers IDDM starts in utero, and znssp2 polypeptide is a developmental gene involved in cell partitioning. Assays and animal models are known in the art for monitoring the exocrine/neuroendocrine cell lineage decision, for observing pancreatic cell balance and for evaluating znssp2 polypeptide, fragment, fusion protein, antibody, agonist or antagonist in the prevention or treatment of the conditions set forth above.

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a znssp2 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 µg/kg of patient weight per day, preferably 0.5–20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of znssp2 is an amount sufficient to produce a clinically significant change in disorders such as, diabetes, autoimmunity, cancer, as well as disorders of the digestive system including, Crohn's disease, ulcerative colitis, pancreatitis, digestive enzymatic disfunction, and cancer suppression and ablation. Similarly, a therapeutically effective amount of znssp2 is an amount sufficient to produce a clinically significant change in disorders accociated with heart, placenta, lung, skeleton muscle, kidney, spleen, prostate, small intestine, colon, peripheral leukocyte, stomach, thyroid, spinal cord, lymph node, trachea, bone marrow, bladder, breast, prostate, and myometrium.

The invention is further illustrated by the following non-limiting examples.

EXAMPLES

Example 1

Extension of EST Sequence

The novel znssp2 polypeptide-encoding polynucleotides of the present invention were initially identified by querying an EST database. A cDNA clone, corresponding to an EST was obtained and the deduced amino acid sequence was determined to be incomplete at the 5' terminal. Nested 5' RACE polymerase chain reactions were performed. The first RACE used primers ZC9719 (SEQ ID NO:8) and ZC17035 (SEQ ID NO:9) and thermolcycler conditions as follows: one cycle at 94° C. for 2 minutes; followed by twenty-five cycles at 94° C. for 20 seconds, 65° C. for 30 seconds, 72° C. for 45 seconds, followed by one cycle at 72° C. for 2 minutes. Bone marrow marathon cDNA was used as a template. The second, nested, RACE reaction used primers ZC9739 (SEQ ID NO:10) and ZCI7036 (SEQ ID NO:11) and thermolcycler conditions as follows: one cycle at 94° C. for 2 minutes; followed by five cycles at 94° C. for 20 seconds, 69° C. for 45; followed by twenty-eight cycles 94° C. for 20 seconds, 64° C. for 30 seconds, 72° C. for 45 seconds, followed by one cycle at 72° C. for 7 minutes. Thus, the 5' terminal of the polynucleotide sequence was elucidated. In order to subclone the 5' portion of the polynucleotide in to a pCR2.1 cloning vector, TA Cloning Kit (Invitrogen, Carlsbad, Calif.), oligonucleotides ZC18227 (SEQ ID NO:4) and ZC17035 (SEQ ID NO:5), designed to the final 5' terminal of the polynucleotide sequence and the original EST clone, respectively, were used as primers. Marathon cDNA prepared from bone marrow was used as a template. Thermocycler conditions were as follows: one cycle at 94° C. for 2 minutes; followed by thirty cycles at 94° C. for 20 seconds, 65° C. for 30 seconds, 72° C. for 30 seconds, followed by one cycle at 72° C. for 5 minutes. The resulting PCR products were gel-purified, subcloned, and sequenced. A consensus sequence was generated by combining the sequence from the PCR products with the cDNA sequence from the EST clone.

Polymorphisms were evident in the consensus sequence at the following positions: R at nucleotide positions 172 and 509, and M at nucleotide position 700; where R is G or A, and M is C or A. A version of the consensus sequence, with a G chosen at position 172 and an A at position 700, was joined to the original EST clone. Thus, amino acid residue 137 of SEQ ID NO:2 is either glycine or serine.

Example 2

Tissue Distribution

Analysis of tissue distribution was performed by the Northern blotting technique using Human Multiple Tissue and Master Dot Blots (Clontech, Palo Alto, Calif.). A 134 bp probe was obtained by PCR of the original EST template using primers ZC16893 (SEQ ID NO:6) and ZC16894 (SEQ ID NO:7). Thermocycler conditions were as follows: one cycle at 94° C. for 2 minutes; followed by thirty cycles at 94° C. for 20 seconds, 65° C. for 30 seconds, 72° C. for 30 seconds, followed by one cycle at 72° C. for 2 minutes. The PCR product was random prime labeled with $^{32}$P using a commercially available kit (Rediprime DNA Labeling System; Amersham Corp., Arlington Heights, Ill.) according to the manufacturer's direction. The probe was then purified using a NucTrap® probe purification column (Stratagene, La Jolla, Calif.). ExpressHyb™ Hybridization Solution (Clontech, Palo Alto, Calif.) was used for pre-hybridization and hybridization. Hybridization took place overnight at 65° C., and the blots were then washed four times in 2×SSC and 0.05% SDS at 50° C., followed by washing twice in 0.1× SSC and 0.1% SDS at 50° C., and developed. Transcripts of about 1.2 kb, 2.8 kb, 4.5 kb and 7.0 kb showed very strong signals in pancreas. Longer exposure indicates that mRNA (of about 1.8 kb) is also present in tissues including heart, placenta, lung, skeleton muscle, kidney, spleen, prostate, small intestine, colon, peripheral leukocyte, stomach, thyroid, spinal cord, lymph node, trachea, and bone marrow.

Example 3

Chromosomal Assignment and Placement of znssp2.

Znssp2 was mapped to chromosome 19 using the commercially available version of the "Stanford G3 Radiation Hybrid Mapping Panel" (Research Genetics, Inc., Huntsville, Ala.). The "Stanford G3 RH Panel" contains PCRable DNAs from each of 83 radiation hybrid clones of the whole human genome, plus two control DNAs (the RM donor and the A3 recipient). A publicly available WWW server (http://shgc-www.stanford.edu) allows chromosomal localization of markers.

For the mapping of znssp2 with the "Stanford G3 RH Panel", 20 μl reactions were set up in a 96-well microtiter plate used for PCR (Stratagene, La Jolla, Calif.) and used in a "RoboCycler Gradient 96" thermal cycler (Stratagene). Each of the 85 PCR reactions consisted of 2 μl 10×KlenTaq PCR reaction buffer (CLONTECH Laboratories, Inc., Palo Alto, Calif.), 1.6 μl dNTPs mix (2.5 mM each, PERKIN-ELMER, Foster City, Calif.), 1 μl sense primer, ZC 19,140 (SEQ ID NO:17), 1 μl antisense primer, ZC 19,141 (SEQ ID NO:18), 2 μl "RediLoad" (Research Genetics, Inc., Huntsville, Ala.), 0.4 μl 50×Advantage KlenTaq Polymerase Mix (Clontech Laboratories, Inc.), 25 ng of DNA from an individual hybrid clone or control and ddH$_2$O for a total volume of 20 μl. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 64° C. and 1 minute AND 15 seconds extension at 72° C., followed by a final 1 cycle extension of 7 minutes at 72° C. The reactions were separated by electrophoresis on a 2% agarose gel (Life Technologies, Gaithersburg, Md.).

The results showed linkage of znssp2 to the framework marker SHGC-33470 with a LOD score of >15 and at a distance of 3.85 cR__10000 from the marker. The use of surrounding markers positions znssp2 in the 19q13 region on the integrated LDB chromosome 19 map (The Genetic Location Database, University of Southhampton).

Example 4

Construct for generating znssp2h Transgenic Mice

Oligonucleotides were designed to generate a PCR fragment containing a consensus Kozak sequence and the exact znssp2 human (znssp2h) coding region (nucleotides 101 to 1294 of SEQ ID NO:1 ). These oligonucleotides were designed with an PmeI site at the 5' end and an AscI site at the 3' end to facilitate cloning into pTg12 -8, our standard transgenic vector. PTg12–8 contains the mouse MT-1 promoter and a 5' rat insulin II intron upstream of the PmeI site.

A full-length clone of znssp2h was generated by the ligation: A sequencing vector containing a znssp2h DNA segment from nucleotide 1 to nucleotide 696 of SEQ ID NO:1, (with the addition of the EcoRI site at the 5' end) was digested from the sequencing vector as an EcoRI/SpeI fragment. Similarly, a sequencing vector containing a znssp2h DNA segment from nucleotide 691 to 1359 of SEQ ID NO:1 was digested from the sequencing vector as a SpeI/NaeI fragment. These digested fragments were ligated to a pre-digested (EcoRI/HincII) pUC19 cloning vector. The NaeI-HincII sites were destroyed in this ligation. A glycine residue was used at position 137 of SEQ ID NO:2.

About one microliter of the ligation reaction was electroporated into DH10B ElectroMax™ competent cells (GIBCO BRL, Gaithersburg, Md.) according to manufacturer's direction and plated onto LB plates containing 100 µg/ml ampicillin, and incubated overnight. Colonies were picked and grown in LB media containing 100 µg/ml ampicillin. Miniprep DNA was prepared from the picked clones and screened for the znssp2h insert by restriction digestion with EcoRI, and subsequent agarose gel electrophoresis.

A polymerase chain reaction using the this full-length sequence as template (200 ng) was used to add a PmeI restriction site and a Kozak sequence (oligonucleotide ZC20336, SEQ ID NO:15) to the 5' end of the znssp2h sequence and an AscI site to the 3' end (oligonucleotide ZC20316, SEQ ID NO:16). PCR reaction conditions were as follows: 95° C. for 5 minutes, wherein Advantage cDNA polymerase (Clontech) was added; 15 cycles of 95° C. for 60 seconds, 62° C. for 60 seconds, and 72° C. for 90 seconds; and 72° C. for 7 minutes. PCR products were separated by agarose gel electrophoresis and purified using a QiaQuick™ (Qiagen) gel extraction kit. The isolated, 1194 bp, DNA fragment was digested with PmeI and AscI (New England Biolabs), ethanol precipitated and ligated into pTg12-8 that was previously digested with PmeI and AscI. The pTg12-8 plasmid, designed for expression of a gene of interest in transgenic mice, contains an expression cassette flanked by 10 kb of MT-1 5' DNA and 7 kb of MT-1 3' DNA. The expression cassette comprises the MT-1 promoter, the rat insulin II intron, a polylinker for the insertion of the desired clone, and the human growth hormone poly A sequence.

About one microliter of the ligation reaction was electroporated as described above. Colonies were picked and grown in LB media containing 100 µg/ml ampicillin. Miniprep DNA was prepared from the picked clones and screened for the znssp2h insert by restriction digestion with EcoRi. Maxipreps of the correct pTg12-8-znssp2h construct were performed and digested with SalI. The SalI fragment fragment containing with 5' and 3' flanking sequences, the MT-1 promoter, the rat insulin II intron, znssp2h cDNA and the human growth hormone poly A sequence was prepared to be used for microinjection into fertilized murine oocytes.

Example 5

Cloning of the mouse ortholog

The human znssp2 gene was used to query the mouse EST database for orthologs. A cDNA clone corresponding to the human znssp2 sequence was obtained and the deduced amino acid sequence was determined to be full-length and a murine ortholog of human znssp2 (znssp2-m). The polynucleotide and polypeptide sequences of the mouse ortholog are shown in SEQ ID NOs:12 and 13. The degenerate sequence for the mouse ortholog is shown in SEQ ID NO:14.

Example 6

Identification of cells expressing znssp2 using in situ hybridization

Human pancreas tissues were isolated and screened for znssp2 expression by in situ hybridization. The human tissues prepared, sectioned and subjected to in situ hybridization included pancreases from normal and pancreatitis patients. The tissues were fixed in 10% buffered formalin and blocked in paraffin using standard techniques. Tissues were sectioned at 4 to 8 microns. Tissues were prepared using a standard protocol ("Development of non-isotopic in situ hybridization"). Briefly, tissue sections were deparaffinized with HistoClear (National Diagnostics, Atlanta, Ga.) and then dehydrated with ethanol. Next they were digested with Proteinase K (50 µg/ml) (Boehringer Diagnostics, Indianapolis, Ind.) at 37° C. for 3 to 5 minutes. This step was followed by acetylation and re-hydration of the tissues.

An in situ probe generated by PCR was designed against the human znssp2 sequence. A set of oligos were designed to generate probes for separate regions of the znssp2 cDNA: Oligos ZC25,177 (SEQ ID NO: 19) and ZC25,232 (SEQ ID NO:20) were used to generate a 551 bp probe for znssp2. The antisense oligo from the PCR primer set also contained the working sequence for the T7 RNA polymerase promoter to allow for easy transcription of antisense RNA probes from these PCR products. The PCR reaction conditions were as follows: 35 cycles at 94° C. for 30 sec, 45° C. for 1 min., 72° C. for 1 min with 5% Dimethyl Sulpnoxide (DMSO) (Sigma Chemical Co, Mo.). The PCR product was purified by Qiagen spin columns followed by phenol/chloroform extraction and ethanol precipitation. The probe was subsequently labeled with digoxigenin (Boehringer) or biotin (Boehringer) using an In Vitro transcription System (Promega, Madison, Wis.) as per manufacturer's instruction.

In situ hybridization was performed with a digoxigenin- or biotin-labeled znssp2 probe (above). The probe was added to the slides at a concentration of 1 to 5 pmol/ml for 12 to 16 hours at 55–60° C. Slides were subsequently washed in 2×SSC and 0.1×SSC at 50–55° C. The signals were amplified using tyramide signal amplification (TSA) (TSA, in situ indirect kit; NEN) and visualized with Vector Red substrate kit (Vector Lab) as per manufacturer's instructions. The slides were then counter-stained with hematoxylin (Vector Laboratories, Burlingame, Calif.).

A signal was seen in both normal and pancreatitis pancreas. The positive-staining cells appeared to be acinar and related cells.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polynucleotide encoding a polypeptide wherein the polypeptide comprises residues 19 to 397 SEQ ID NO:2.

2. The isolated polynucleotide according to claim 1, wherein the polypeptide molecule comprises residues 1 to 397 of SEQ ID NO:2.

3. An isolated polynucleotide encoding a polypeptide molecule wherein the polypeptide is selected from the group consisting of;
   a) a polypeptide consisting of residues 1 to 18 of SEQ ID NO:2;
   b) a polypeptide consisting of residues 19 to 147 of SEQ ID NO:2;
   c) a polypeptide comprising residues 19 to 397 of SEQ ID NO:2; and
   d) a polypeptide comprising residues 1 to 397 of SEQ ID NO:2.

4. An expression vector comprising the following operably linked elements:
   a transcription promoter;
   a DNA segment wherein the DNA segment is the polynucleotide according to claim 1, and
   a transcription terminator.

5. The expression vector according to claim 4 wherein the DNA segment additionally encodes an affinity tag.

6. A cultured cell transformed with an expression vector according to claim 4, wherein said cell expresses the polypeptide encoded by the DNA segment.

7. A method of producing a polypeptide comprising culturing a cell according to claim 6, whereby said cell expresses the polypeptide encoded by the DNA segment; and recovering the polypeptide.

* * * * *